US012790597B2

(12) United States Patent
Cuero Rengifo

(10) Patent No.: US 12,790,597 B2
(45) Date of Patent: Nov. 10, 2026

(54) BIOLOGICAL DEVICES FOR THE DETECTION AND CATABOLISM OF ALCOHOL AND OPIOIDS AND METHODS OF USE THEREOF

(71) Applicant: Bio Capital Holdings, LLC, Houston, TX (US)

(72) Inventor: Raul Cuero Rengifo, Cypress, TX (US)

(73) Assignee: Bio Capital Holdings, LLC, Houston, TX (US)

( * ) Notice: Subject to any disclaimer, the term of this patent is extended or adjusted under 35 U.S.C. 154(b) by 79 days.

(21) Appl. No.: 19/013,058

(22) Filed: Jan. 8, 2025

(65) Prior Publication Data

US 2025/0230420 A1 Jul. 17, 2025

Related U.S. Application Data

(60) Provisional application No. 63/619,814, filed on Jan. 11, 2024.

(51) Int. Cl.

| | |
|---|---|
| ***C12N 9/04*** | (2006.01) |
| ***C12N 9/02*** | (2006.01) |
| ***C12N 9/10*** | (2006.01) |
| ***C12N 15/81*** | (2006.01) |

(52) U.S. Cl.

CPC ......... *C12N 9/0006* (2013.01); *C12N 9/0071* (2013.01); *C12N 9/1051* (2013.01); *C12N 9/13* (2013.01); *C12N 15/81* (2013.01); *C12Y 101/01001* (2013.01); *C12Y 114/14001* (2013.01); *C12Y 204/01017* (2013.01); *C12Y 204/01255* (2013.01); *C12Y 208/02001* (2013.01)

(58) Field of Classification Search

CPC .. C12N 9/0006; C12N 9/0071; C12N 9/1051; C12N 9/13; C12N 15/81; C12Y 101/01001; C12Y 114/14001; C12Y 204/01017; C12Y 204/01255; C12Y 208/02001

See application file for complete search history.

(56) References Cited

FOREIGN PATENT DOCUMENTS

WO WO-0218554 A2 * 3/2002 .............. A61P 35/00

OTHER PUBLICATIONS

Ikushiro et al. "Functional co-expression of xenobiotic metabolizing enzymes, rat cytochrome P450 1A1 and UDP-glucuronosyltransferase 1A6, in yeast microsomes" Biochimica et Biophysica Acta 1672 (2004) 86-92 (Year: 2004).*

Benedetti et al. "Involvement of enzymes other than CYPs in the oxidative metabolism of xenobiotics" Expert Opinion on Drug Metabolism & Toxicology (2006) 2(6):895-921 (Year: 2006).*

Zhang et al. "Phase I to II cross-induction of xenobiotic metabolizing enzymes: A feedforward control mechanism for potential hormetic responses" Toxicology and Applied Pharmacology 237 (2009) 345-356 (Year: 2009).*

* cited by examiner

*Primary Examiner* — Thane Underdahl

(74) *Attorney, Agent, or Firm* — Thomas | Horstemeyer, LLP

(57) ABSTRACT

Described herein are biological devices and extracts useful for detecting alcohol and/or opioids in a biological sample from a subject; the biological devices and extracts can also be useful for detoxifying alcohol and/or opioids in a subject in need thereof. The biological devices include microbial cells transformed with a DNA construct containing genes for producing sulfotransferase, UDP-glucuronosyltransferase, O-linked N-acetylglucosamine transferase, alcohol dehydrogenase, and cytochrome P450. In some instances, the biological devices also include a gene for enhanced green fluorescent protein. Methods for using the devices are also provided herein.

30 Claims, 2 Drawing Sheets

Specification includes a Sequence Listing.

BIOLOGICAL DEVICES FOR THE DETECTION AND CATABOLISM OF ALCOHOL AND OPIOIDS AND METHODS OF USE THEREOF

CROSS-REFERENCE TO RELATED APPLICATIONS

This application claims the benefit of U.S. Provisional Application Ser. No. 63/619,814, filed Jan. 11, 2024, which is incorporated herein by reference in its entirety.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The sequence listing in written computer readable format (CRF) as a text file named "930201-8120_Sequence_Listing.xml" created on Dec. 11, 2023, and having a size of 33,987 bytes, is incorporated by reference in its entirety.

BACKGROUND

As many as 29.5 million people in the United States experienced alcohol use disorder in the year 2022. Excessive alcohol use can lead to injuries, violence, alcohol poisoning, risky behaviors, miscarriage and/or stillbirth, and death, as well as chronic health conditions including various cancers, cardiovascular diseases, gastrointestinal disorders, and diseases and disorders of the central nervous system (e.g. dementia, learning and memory problems, depression, anxiety, and more).

Although opioids are commonly prescribed pain medications, over 600,000 people have died from opioid overdoses in the past 20 years, including from prescription opioids, street drugs such as heroin, and synthetic opioids including fentanyl. Opioid abuse can lead to changes in mood or personality, financial hardship, lost jobs and/or penalties for missed school, legal troubles, and the like, and illegally manufactured synthetic opioids can be contaminated or deliberately mixed with other dangerous substances, leading to potentially lethal health effects.

Healthcare professionals have a need to assess patients fully, quickly, and correctly, including in emergency situations, such as an overdose, when the patients may not be able to communicate, in order to offer effective treatment. In some situations, that may mean administering emergency medications to metabolize or block the effects of opioids (as with naloxone) or alcohol on the brain and body.

It would thus be desirable to develop an inexpensive, safe, and easy-to-use system for identifying alcohol, opioids, and/or their metabolites in a biological sample from a patient. It would further be desirable to develop such a system for the detoxification of alcohol and/or opioids. These and other needs are satisfied by the present disclosure.

SUMMARY

Described herein are biological devices and extracts useful for detecting alcohol and/or opioids in a biological sample from a subject; the biological devices and extracts can also be useful for detoxifying alcohol and/or opioids in a subject in need thereof. The biological devices include microbial cells transformed with a DNA construct containing genes for producing sulfotransferases, UDP-glucuronosyltransferase, O-linked N-acetylglucosamine transferase, alcohol dehydrogenase, and cytochrome P450. In some instances, the biological devices also include a gene for enhanced green fluorescent protein. Methods for using the devices are also provided herein.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

Many aspects of the present disclosure can be better understood with reference to the following drawings, which are incorporated in and constitute a part of this specification. The components in the drawings are not necessarily to scale, emphasis instead being placed upon clearly illustrating the principles of the present disclosure.

Figure 1A:
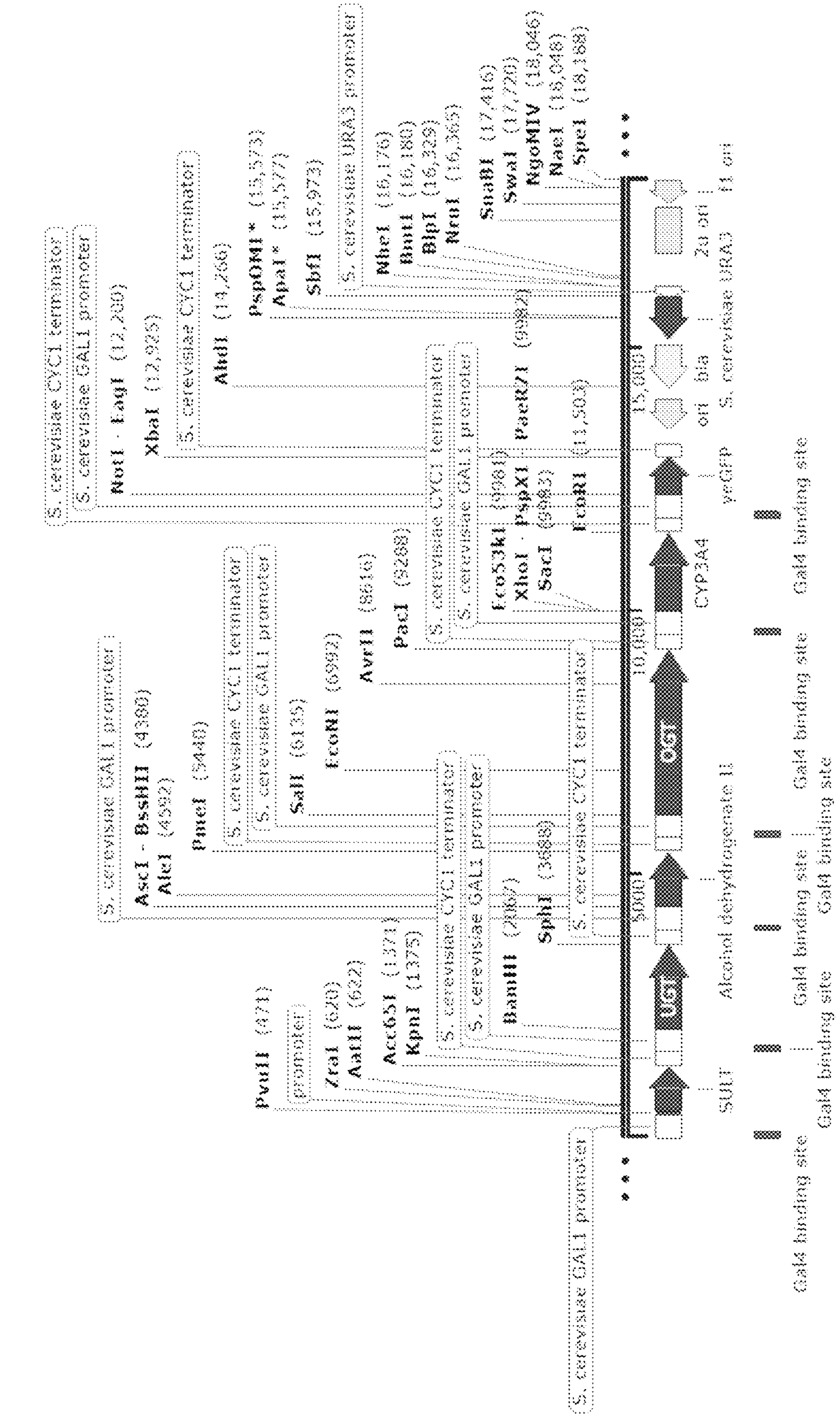
FIGS. 1A-1B show, respectively, linear and circular maps of an exemplary biological device.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Disclosed herein are DNA constructs containing the following genetic components:

(a) a gene that encodes sulfotransferase;

(b) a gene that encodes UDP-glucuronosyltransferase (UGT);

(c) a gene that encodes O-linked N-acetylglucosamine transferase (OGT);

(d) a gene that encodes an alcohol dehydrogenase; and (e) a gene that encodes a cytochrome P450.

The DNA constructs may variously encode genes encoding reporter proteins, genes encoding resistance to one or more antibiotics, and the like, and may include regulatory sequences including promoters, terminators, ribosomal binding sites, LAC operons, or other components necessary for the replication of and expression of the genes encoded by the DNA constructs inside microbial hosts such as, for example, *Saccharomyces cerevisiae, Escherichia coli*, and other microorganisms. Also disclosed are vectors including the DNA constructs and biological devices consisting of host cells that include one or more copies of the vectors.

Also disclosed herein are methods for producing a composition useful for the detection of alcohol and/or opioids in a biological sample from a subject, and methods for detoxifying excess amounts of alcohol and/or opioids in a subject. Exemplary methods for producing the compositions are disclosed in the Examples.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall defined to have the following meanings:

It must be noted that, as used in the specification and the appended claims, the singular forms "a," "an," and "the" include plural referents unless the context clearly dictates otherwise. Thus, for example, reference to "a metabolite" includes mixtures of two or more such metabolites, and the like.

"Optional" or "optionally" means that the subsequently described event or circumstance can or cannot occur, and that the description includes instances where the event or circumstance occurs and instances where it does not. For example, the phrase "a microorganism is optionally genetically modified" means that the microorganism may or may not be genetically modified.

An "opioid" as used herein refers to a drug that interacts with opioid receptors. In one aspect, the opioid can be a chemically synthesized narcotic including, but not limited to, acetylpropionylmorphine, desomorphine, dextromethorphan, dextropropoxyphene, diacetyldihydromorphine, dibenzoylmorphine, dipropanoylmorphine, ethylmorphine, loperamide, hydrocodone, hydromorphone, oxycodone, oxymorphone, meperidine, methadone, fentanyl, carfentanyl, pethidine, levorphanol, tramadol, tapentadol, buprenorphine, or any combination thereof. In some aspects, the term "opioid" is used herein to refer to naturally extracted opiates from *Papaver somniferum* such as, for example, opium, morphine, codeine, or heroin.

Throughout this specification, unless the context dictates otherwise, the word "comprise," or variations such as "comprises" or "comprising," will be understood to imply the inclusion of a stated element, integer, step, or group of elements, integers, or steps, but not the exclusion of any other element, integer, step, or group of elements, integers, or steps.

As used herein, the term "about" is used to provide flexibility to a numerical range endpoint by providing that a given numerical value may be "a little above" or "a little below" the endpoint without affecting the desired result. For purposes of the parent disclosure, "about" refers to a range extending from 10% below the numerical value to 10% above the numerical value. For example, if the numerical value is 10, "about 10" means between 9 and 11, inclusive of the endpoints 9 and 11.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y.' The range can also be expressed as an upper limit, e.g. 'about x, y, z, or less' and should be interpreted to include the specific ranges of 'about x,' 'about y', and 'about z' as well as the ranges of 'less than x', less than y', and 'less than z'. Likewise, the phrase 'about x, y, z, or greater' should be interpreted to include the specific ranges of 'about x,' 'about y,' and 'about z' as well as the ranges of 'greater than x,' greater than y,' and 'greater than z.' In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed that while specific reference to each various individual and collective combination and permutation of these compounds may not be explicitly disclosed, each is specifically contemplated and described herein. For example, if a UDP-glucuronosyltransferase (UGT) is disclosed and discussed and a number of different substrates on which the UGT can act are discussed, each and every combination and permutation of UGT and substrate that is possible is specifically contemplated unless specifically indicated to the contrary. For example, if a class of molecules A, B, and C are disclosed as well as a class of molecules D, E, and F, and an example of a combination molecule, A-D, is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of elements of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a composition containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

DNA Constructs and Biological Devices

In one aspect, cells transformed with a DNA construct can be used in the methods described herein. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning two sequences so that the homology is at its highest level. Another way of calculating homology can be performed according to published algorithms (see Zuker, M., *Science,* 244:48-52, 1989; Jaeger et al, *Proc. Natl. Acad. Sci. USA,* 86:7706-7710, 1989; Jaeger et al, *Methods Enzymol.,* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least about 70%, about 75%, about 80%, about 85%, about 90%, about 95%, or about 99% homology to a particular sequence wherein the variants are conservative or silent mutations. It is understood that any of the sequences described herein can be a variant or derivative having the homology values listed above.

In some aspects, genes of interest can be spliced into suitable vectors using restriction enzymes and/or other techniques known in the art. Further in this aspect, synthesis and/or isolation of the genes of interest prior to inclusion in the disclosed constructs may result in the addition of C-terminal and/or N-terminal sequence data including, but not limited to, restriction enzyme recognition sites, linking bases, short segments of chromosomal DNA (including introns or portions of introns if the sequences originate from eukaryotic cells), transposons, nucleotide repeats, regulatory sequences, and/or other material that do not contribute to the known structure of the expressed protein, or are not part of the expressed protein's active site. In one aspect, presence of these remnants may lead to somewhat reduced homology with respect to gene sequence, but the DNA constructs encoding the same can still produce proteins having the desired sequence, active site, and function.

In another aspect, many eukaryotic genes include introns and mRNAs produced during transcription of the same can be spliced differently, producing several transcript variants from the same gene but having slightly different sequences (i.e., reduced levels of homology). In one aspect, different transcript variants can produce proteins having the same active site but differing in another way (e.g. in C-terminal or N-terminal sequence, affecting assembly of protein subunits or other folding processes, cellular localization of the peptides or proteins, or activity level of the peptides or proteins produced due to differential regulation, or the like.

In one aspect, a database such as, for example, GenBank, can be used to determine the sequences of genes and/or regulatory regions of interest, the species from which these elements originate, and related homologous sequences.

In one aspect, the nucleic acids used in the DNA constructs described herein can be amplified using polymerase chain reaction (PCR) prior to being ligated into a plasmid or other vector. Typically, PCR-amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or genes. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

Alcohol- and Opioid-Related DNA Constructs

In one aspect, provided herein are DNA constructs having at least the following genetic components:

(a) a gene that encodes a sulfotransferase;

(b) a gene that encodes UGT;

(c) a gene that encodes OGT;

(d) a gene that encodes an alcohol dehydrogenase; and (e) a gene that encodes cytochrome P450.

Each component of the DNA constructs is described in detail below.

In one aspect, the DNA constructs disclosed herein incorporate a gene that encodes sulfotransferase. In a further aspect, sulfotransferase is an enzyme that catalyzes the transfer of a sulfo group from a donor molecule to an alcohol or amine, wherein the molecule to be modified can be part of numerous different biomolecules including proteins, lipids, and/or carbohydrates. Sulfotransferase enzymes are involved in drug metabolism and may be cytosolic or membrane-associated.

In one aspect, the gene that encodes sulfotransferase is isolated from a mammal such as, for example, human, bonobo, Western lowland gorilla, chimpanzee, Bornean orangutan, Northern white-cheeked gibbon, Sumatran orangutan, silvery gibbon, siamang, golden snub-nosed monkey, Indochinese rhesus macaque, crab-eating macaque, Tibetan macaque, Southern pig-tailed macaque, drill, green monkey, Ugandan red colobus, Angola colobus, Francois' langur, olive baboon, black-and-white snub-nosed monkey, sooty mangabey, black-capped squirrel monkey, common marmoset, gelada, Panamanian white-faced capuchin, South-central black rhinoceros, plains zebra, Philippine tarsier, Southern white rhinoceros, African wild ass, horse, Przewalski's horse, Sunda slow loris, Northern greater galago, elk, Coquerel's sifaka, dwarf musk deer, red deer, Chinese tree shrew, tufted capuchin, goat, ring-tailed lemur, sheep, scimitar oryx, carabao, takin, Eastern gray squirrel, creeping vole, lesser Egyptian jerboa, hybrid cattle, or cattle. In a further aspect, the gene that encodes sulfotransferase has SEQ ID NO. 1 or at least 70% homology thereto, at least 75% homology thereto, at least 80% homology thereto, at least 85% homology thereto, at least 90% homology thereto, at least 95% homology thereto, or at least 99% homology thereto.

Other sequences encoding sulfotransferase or related or homologous genes can be identified in a database such as, for example, GenBank. In one aspect, the gene that encodes sulfotransferase is isolated from *Homo sapiens* and can be identified by the GI number DQ891165.2 in the GenBank database. In another aspect, sequences useful herein include those with GI numbers listed in Table 1:

TABLE 1

| Sulfotransferase | | |
|---|---|---|
| Source Organism | Sequence Description | GI Number |
| synthetic construct | Cytosolic sulfotransferase family 2A | DQ891165.2 |
| *Homo sapiens* | Sulfotransferase family 2A | NM_003167.4 |
| *Homo sapiens* | Cytosolic sulfotransferase family 2A | AK313415.1 |
| *Homo sapiens* | Cytosolic sulfotransferase family 2A | AK289380.1 |
| *Homo sapiens* | Cytosolic sulfotransferase family 2A | BC020755.1 |
| *Homo sapiens* | Hydroxysteroid sulfotransferase | X84816.1 |
| *Homo sapiens* | Dehydroepiandrosterone sulfotransferase | U08025.1 |
| *Homo sapiens* | Dehydroepiandrosterone sulfotransferase | U08024.1 |
| synthetic construct | Cytosolic sulfotransferase family 2A | DQ894346.2 |
| synthetic construct | Cytosolic sulfotransferase family 2A | AY893804.1 |
| *Homo sapiens* | Dehydroepiandrosterone sulfotransferase | X70222.1 |
| *Homo sapiens* | Dehydroepiandrosterone sulfotransferase | L20000.1 |
| synthetic construct | Dehydroepiandrosterone sulfotransferase | AY891264.1 |
| *Homo sapiens* | Sulfotransferase-related | L02337.1 |
| *Pan paniscus* | Sulfotransferase family 2A | XM_003814106.5 |
| *synthetic construct* | Synthetic construct | CU676701.1 |
| *Gorilla gorilla gorilla* | Sulfotransferase family 2A | XM_019014383.3 |
| *Pan troglodytes* | Sulfotransferase family 2A | XM_016936354.3 |
| synthetic construct | Synthetic construct | CU676700.1 |
| *Pongo pygmaeus* | Sulfotransferase family 2A | XM_054465737.1 |
| *Nomascus leucogenys* | Sulfotransferase family 2A | XM_030796993.1 |
| *Pongo abelii* | Sulfotransferase family 2A | XM_024237305.2 |
| *Hylobates moloch* | Sulfotransferase family 2A | XM_032171519.2 |
| *Symphalangus syndactylus* | Sulfotransferase family 2A | XM_055237877.1 |
| *Rhinopithecus roxellana* | Sulfotransferase family 2A | XM_010377389.2 |
| *Macaca mulatta* | Sulfotransferase family 2A | XM_001113439.4 |
| *Macaca fascicularis* | Sulfotransferase family 2A | NM_001319603.2 |
| *Macaca thibetana thibetana* | Sulfotransferase family 2A | XM_050772329.1 |
| *Macaca fascicularis* | Sulfotransferase family 2A | KJ922611.1 |
| *Macaca nemestrina* | Sulfotransferase family 2A | XM_011736115.1 |
| *Mandrillus leucophaeus* | Cytosolic sulfotransferase family 2A | XM_011969919.1 |
| *Chlorocebus sabaeus* | Sulfotransferase family 2A | XM_007997376.2 |
| *Macaca fascicularis* | Hydroxysteroid sulfotransferase subunit | D85521.1 |
| *Piliocolobus tephrosceles* | Sulfotransferase family 2A | XM_023182589.2 |
| *Colobus angolensis palliatus* | Cytosolic sulfotransferase family 2A | XM_011926333.1 |
| *Trachypithecus francoisi* | Sulfotransferase family 2A | XM_033223840.1 |
| *Homo sapiens* | Hydroxysteroid sulfotransferase | S43861.1 |
| *Papio anubis* | Sulfotransferase family 2A | XM_031659105.1 |
| *Macaca mulatta* | Sulfotransferase family 2A | XM_028839007.1 |
| *Rhinopithecus bieti* | Sulfotransferase family 2A | XM_017888842.1 |
| *Chlorocebus sabaeus* | Sulfotransferase family 2A | XM_007997375.2 |
| *Cercocebus atys* | Cytosolic sulfotransferase family 2A | XM_012080695.1 |
| *Saimiri boliviensis boliviensis* | Sulfotransferase family 2A | XM_039466201.1 |

TABLE 1-continued

| Sulfotransferase | | |
|---|---|---|
| Source Organism | Sequence Description | GI Number |
| *Callithrix jacchus* | Sulfotransferase family 2A | MK948028.1 |
| *Callithrix jacchus* | Sulfotransferase family 2A | XM_035285208.2 |
| *Theropithecus gelada* | Sulfotransferase family 2A | XM_025365864.1 |
| *Cebus imitator* | Sulfotransferase family 2A | XM_017500432.1 |
| *Diceros bicornis minor* | Sulfotransferase 2A1-like | XM_058530721.1 |
| *Equus quagga* | Sulfotransferase 2A1-like | XM_046683999.1 |
| *Carlito syrichta* | Sulfotransferase family 2A | XM_008054161.1 |
| *Ceratotherium simum simum* | Sulfotransferase-like | XM_004440204.2 |
| *Equus quagga* | Sulfotransferase 2A1-like | XM_046680427.1 |
| *Equus asinus* | Sulfotransferase 2A1-like | XM_014852181.2 |
| *Equus asinus* | Sulfotransferase 2A1-like | XM_044759893.1 |
| *Diceros bicornis minor* | Sulfotransferase 2A1-like | XM_058531001.1 |
| *Equus caballus* | Bile salt sulfotransferase | XM_001487980.4 |
| *Equus przewalskii* | Cytosolic sulfotransferase family 2A | XM_008527554.1 |
| *Nycticebus coucang* | Sulfotransferase 2A1-like | XM_053604733.1 |
| *Otolemur garnettii* | Bile salt sulfotransferase-like | XM_003803630.3 |
| *Carlito syrichta* | Bile salt sulfotransferase-like | XM_008070150.1 |
| *Cervus canadensis* | Sulfotransferase 2A1-like | XM_043436571.1 |
| *Propithecus coquereli* | Cytosolic sulfotransferase family 2A | XM_012653482.1 |
| *Saimiri boliviensis boliviensis* | Sulfotransferase 2A1-like | XM_003940301.2 |
| *Equus caballus* | Bile salt sulfotransferase | XM_001917487.3 |
| *Nycticebus coucang* | Sulfotransferase 2A1-like | XM_053604763.1 |
| *Otolemur garnettii* | Bile salt sulfotransferase-like | XM_003803500.3 |
| *Moschus berezovskii* | Sulfotransferase 2A1-like | XM_055411051.1 |
| *Cervus elaphus* | Sulfotransferase 2A1-like | XM_043899653.1 |
| *Tupaia chinensis* | Bile salt sulfotransferase | XM_006142183.3 |
| *Sapajus apella* | Bile salt sulfotransferase-like | XM_032262493.1 |
| *Equus asinus* | Sulfotransferase 2A1-like | XM_014852179.2 |
| *Sapajus apella* | Bile salt sulfotransferase-like | XM_032262506.1 |
| *Nycticebus coucang* | Sulfotransferase 2A1-like | XM_053604746.1 |
| *Nycticebus coucang* | Sulfotransferase 2A1-like | XM_053604745.1 |
| *Nycticebus coucang* | Sulfotransferase 2A1-like | XM_053604744.1 |
| *Otolemur garnettii* | Bile salt sulfotransferase-like | XM_003799563.3 |
| *Capra hircus* | Bile salt sulfotransferase-like | XM_005692671.3 |
| *Equus przewalskii* | Bile salt sulfotransferase-like | XM_008527552.1 |
| *Lemur catta* | Sulfotransferase family 2A | XM_045531292.1 |
| *Ovis aries* | Sulfotransferase 2A1-like | XM_004015342.6 |
| *Oryx dammah* | Sulfotransferase 2A1-like | XM_040252419.1 |
| *Otolemur garnettii* | Bile salt sulfotransferase-like | XM_003803729.3 |
| *Bubalus carabanensis* | Sulfotransferase family 2A | XM_055552249.1 |
| *Nycticebus coucang* | Sulfotransferase 2A1-like | XR_008382983.1 |
| *Nycticebus coucang* | Sulfotransferase 2A1-like | XR_008382982.1 |
| *Nycticebus coucang* | Sulfotransferase 2A1-like | XM_053604751.1 |
| *Budorcas taxicolor* | Sulfotransferase 2A1-like | XM_052656634.1 |
| *Otolemur garnettii* | Bile salt sulfotransferase-like | XM_003803632.2 |
| *Diceros bicornis minor* | Sulfotransferase 2A1-like | XM_058529721.1 |
| *Nycticebus coucang* | Sulfotransferase 2A1-like | XM_053604750.1 |
| *Nycticebus coucang* | Sulfotransferase 2A1-like | XM_053604749.1 |
| *Nycticebus coucang* | Sulfotransferase 2A1-like | XM_053604748.1 |
| *Sciurus carolinensis* | Sulfotransferase 2A1-like | XM_047537850.1 |
| *Microtus oregoni* | Sulfotransferase 2A1-like | XM_041654000.1 |
| *Cervus elaphus* | Sulfotransferase 2A1-like | XM_043899650.1 |
| *Cervus elaphus* | Sulfotransferase 2A1-like | XM_043899649.1 |
| *Jaculus jaculus* | Sulfotransferase 2A1 | XM_004672769.2 |
| *Bos indicus × Bos taurus* | Bile salt sulfotransferase-like | XM_027515315.1 |
| *Bos taurus* | Sulfotransferase 2A1 | XM_005219462.5 |
| *Equus asinus* | Sulfotransferase 2A1-like | XM_044760101.1 |

In one aspect, the DNA constructs disclosed herein incorporate a gene that encodes UDP glucuronosyltransferase. In a further aspect, UDP glucuronosyltransferase is an enzyme found in microsomes that is involved in the elimination of common prescription drugs as well as dietary chemicals, environmental chemicals, toxic substances, and the like. UDP glucuronosyltransferase catalyzes the transfer of a glucuronosyl group from UDP to a substrate containing oxygen, nitrogen, sulfur, or a carboxyl group, producing a polar molecule that can be easily excreted such as, for example, by the kidneys.

In one aspect, the gene that encodes UDP glucuronosyltransferase is isolated from a mammal such as, for example, Human, Northern white-cheeked gibbon, silvery gibbon, Sumatran orangutan, Western lowland gorilla, bonobo, chimpanzee, crab-eating macaque, Southern pig-tailed macaque, Bornean orangutan, gelada, Tibetan macaque, Angola colobus, siamang, olive baboon, black-and-white snub-nosed monkey, Francois' langur, drill, sooty mangabey, Indochinese rhesus macaque, Nancy Ma's night monkey, Panamanian white-faced capuchin, Ugandan red colobus, golden snub-nosed monkey, common marmoset, black-capped squirrel monkey, Philippine tarsier, Daubenton's bat, Southern white rhinoceros, brown bear, polar bear, ferret, European mink, African wild ass, Pacific walrus, Eurasian otter, black-footed ferret, horse, Coquerel's sifaka, Alpine marmot, or domestic water buffalo. In a further aspect, the gene that encodes UDP glucuronosyltransferase has SEQ ID NO. 2 or at least 70% homology thereto, at least 75% homology thereto, at least 80% homology thereto, at least 85% homology thereto, at least 90% homology thereto, at least 95% homology thereto, or at least 99% homology thereto.

Other sequences encoding UDP glucuronosyltransferase or related or homologous genes can be identified in a database such as, for example, GenBank. In one aspect, the gene that encodes UDP glucuronosyl transferase (UGT) is isolated from *Homo sapiens* and can be identified by the GI number KJ899004.1 in the GenBank database. In another aspect, sequences useful herein include those with GI numbers listed in Table 2:

TABLE 2

UDP Glucuronosyl Transferase

| Source Organism | Sequence Description | GI Number |
|---|---|---|
| *Human ORFeome Gateway entry vector* | Synthetic construct | LT741658.1 |
| synthetic construct | UDP glucuronosyltransferase | KJ899004.1 |
| *Homo sapiens* | UDP glucuronosyltransferase | BC139784.1 |
| *Homo sapiens* | UDP glucuronosyltransferase | M57951.1 |
| *Homo sapiens* | UDP glucuronosyltransferase | NM_007120.3 |
| *Homo sapiens* | UDP glucuronosyltransferase | AY435139.1 |
| *Homo sapiens* | UDP glucuronosyltransferase | BC131623.1 |
| *Homo sapiens* | Similar to UDP glucuronosyltransferase | AK313623.1 |
| *Nomascus leucogenys* | UDP glucuronosyltransferase | XM_012501123.2 |
| *Nomascus leucogenys* | UDP glucuronosyltransferase | XM_012501124.2 |
| *Hylobates moloch* | UDP glucuronosyltransferase | XM_032753698.2 |
| *Pongo abelii* | UDP glucuronosyltransferase | XM_054548631.1 |
| *Hylobates moloch* | UDP glucuronosyltransferase | XM_032753690.1 |
| *Pongo abelii* | UDP glucuronosyltransferase | NM_001132143.2 |
| *Pongo abelii* | Genomic DNA | CR858865.1 |
| *Homo sapiens* | UDP glucuronosyltransferase | NM_019093.4 |
| synthetic construct | UDP glucuronosyltransferase | BC166641.1 |
| *Homo sapiens* | UDP glucuronosyltransferase | AY435138.1 |
| *Gorilla gorilla gorilla* | UDP glucuronosyltransferase | XM_031008569.2 |
| *Pan paniscus* | UDP glucuronosyltransferase | XM_057301548.1 |
| *Nomascus leucogenys* | UDP glucuronosyltransferase | XM_030803040.1 |
| *Pan troglodytes* | UDP glucuronosyltransferase | XM_001151100.7 |
| *Macaca fascicularis* | UDP glucuronosyltransferase | KJ922576.1 |
| *Macaca fascicularis* | UDP glucuronosyltransferase | NM_001350029.1 |
| *Pongo abelii* | UDP glucuronosyltransferase | XM_009238249.3 |
| *Homo sapiens* | UDP glucuronosyltransferase | NM_019078.2 |
| synthetic construct | UDP glucuronosyltransferase | BC141470.1 |
| *Homo sapiens* | UDP glucuronosyltransferase | AY435140.1 |
| *Macaca fascicularis* | UDP glucuronosyltransferase | KJ922577.1 |
| *Macaca nemestrina* | UDP glucuronosyltransferase | XM_011728056.2 |
| *Pongo pygmaeus* | UDP glucuronosyltransferase | XM_054479029.1 |
| *Theropithecus gelada* | UDP glucuronosyltransferase | XM_025404577.1 |
| *Macaca thibetana thibetana* | UDP glucuronosyltransferase | XM_050752685.1 |
| *Colobus angolensis palliatus* | UDP glucuronosyltransferase | XM_011929635.1 |
| *Symphalangus syndactylus* | UDP glucuronosyltransferase | XM_055291039.1 |
| *Papio anubis* | UDP glucuronosyltransferase | NM_001112619.2 |
| *Papio anubis* | UDP glucuronosyltransferase | DQ355194.1 |
| *Rhinopithecus bieti* | UDP glucuronosyltransferase | XM_017890366.1 |
| *Pan paniscus* | UDP glucuronosyltransferase | XM_008965704.5 |
| *Gorilla gorilla gorilla* | UDP glucuronosyltransferase | XM_019022564.3 |
| *Pan troglodytes* | UDP glucuronosyltransferase | XM_003949993.5 |
| *Trachypithecus francoisi* | UDP glucuronosyltransferase | XM_033229825.1 |
| *Homo sapiens* | UDP glucuronosyltransferase | DQ364249.1 |
| *Macaca fascicularis* | UDP glucuronosyltransferase | KJ922579.1 |
| *Macaca fascicularis* | UDP glucuronosyltransferase | KJ922578.1 |
| *Papio anubis* | UDP glycosyl transferase | NM_001112620.2 |
| *Mandrillus leucophaeus* | UDP glucuronosyltransferase | XM_011980258.1 |
| *Papio anubis* | UDP glycosyl transferase | DQ355195.1 |
| *Macaca fascicularis* | UDP glucuronosyltransferase | KJ922580.1 |
| *Cercocebus atys* | UDP glucuronosyltransferase | XM_012044381.1 |
| *Macaca fascicularis* | UDP glucuronosyltransferase | KJ922575.1 |
| *Macaca mulatta* | UDP glucuronosyltransferase | XM_015111222.2 |
| *Papio anubis* | UDP glycosyl transferase | NM_001112658.1 |
| *Theropithecus gelada* | UDP glucuronosyltransferase | XM_025404579.1 |
| synthetic construct | UDP glucuronosyltransferase | KJ902675.1 |
| *Homo sapiens* | UDP glucuronosyltransferase | BC121036.1 |
| *Macaca thibetana thibetana* | UDP glucuronosyltransferase | XM_050752684.1 |
| *Trachypithecus francoisi* | UDP glucuronosyltransferase | XM_033229826.1 |
| *Colobus angolensis palliatus* | UDP glucuronosyltransferase | XM_011929634.1 |
| *Papio anubis* | UDP glycosyl transferase | NM_001112657.1 |
| *Aotus nancymaae* | UDP glucuronosyltransferase | XM_012434161.2 |
| *Cebus imitator* | UDP glucuronosyltransferase | XM_017537702.2 |
| *Piliocolobus tephrosceles* | UDP glucuronosyltransferase | XM_023228756.2 |
| *Rhinopithecus roxellana* | UDP glucuronosyltransferase | XM_010368431.2 |
| *Cebus imitator* | UDP glucuronosyltransferase | XM_037741748.1 |
| *Macaca thibetana thibetana* | UDP glucuronosyltransferase | XM_050752686.1 |
| *Rhinopithecus bieti* | UDP glucuronosyltransferase | XM_017890367.1 |

TABLE 2-continued

| UDP Glucuronosyl Transferase | | |
|---|---|---|
| Source Organism | Sequence Description | GI Number |
| *Cebus imitator* | UDP glucuronosyltransferase | XM_017537700.2 |
| *Aotus nancymaae* | UDP glucuronosyltransferase | XM_012434160.2 |
| *Callithrix jacchus* | UDP glucuronosyltransferase | XM_008999721.3 |
| *Callithrix jacchus* | UDP glucuronosyltransferase | XM_008999722.3 |
| *Callithrix jacchus* | UDP glucuronosyltransferase | MF457777.1 |
| *Rhinopithecus roxellana* | UDP glucuronosyltransferase | XM_010368434.2 |
| *Callithrix jacchus* | UDP glucuronosyltransferase | MK948017.1 |
| *Saimiri boliviensis boliviensis* | UDP glucuronosyltransferase | XM_039469813.1 |
| *Carlito syrichta* | UDP glucuronosyltransferase | XM_008056106.2 |
| *Gorilla gorilla gorilla* | UDP glucuronosyltransferase | XM_055379832.1 |
| *Theropithecus gelada* | UDP glucuronosyltransferase | XM_025404583.1 |
| *Nomascus leucogenys* | UDP glucuronosyltransferase | XM_012501144.2 |
| *Mandrillus leucophaeus* | UDP glucuronosyltransferase | XM_011980264.1 |
| *Mandrillus leucophaeus* | UDP glucuronosyltransferase | XM_011980263.1 |
| *Rhinopithecus roxellana* | UDP glucuronosyltransferase | XM_010368465.2 |
| *Theropithecus gelada* | UDP glucuronosyltransferase | XM_025404585.1 |
| *Cercocebus atys* | UDP glucuronosyltransferase | XM_012044424.1 |
| *Myotis daubentonii* | UDP glucuronosyltransferase | XM_059703601.1 |
| *Ceratotherium simum simum* | UDP glucuronosyltransferase | XM_014785409.1 |
| *Piliocolobus tephrosceles* | UDP glucuronosyltransferase | XM_023228758.3 |
| *Ursus arctos* | UDP glucuronosyltransferase-like | XM_044380685.3 |
| *Ursus maritimus* | UDP glucuronosyltransferase-like | XM_008690307.2 |
| *Mustela putorius furo* | UDP glucuronosyltransferase | XM_045066748.1 |
| *Mustela lutreola* | UDP glucuronosyltransferase-like | XM_059167659.1 |
| *Equus asinus* | UDP glucuronosyltransferase-like | XM_014862572.2 |
| *Odobenus rosmarus divergens* | UDP glucuronosyltransferase | XM_004396069.2 |
| *Lutra lutra* | UDP glucuronosyltransferase-like | XM_047721420.1 |
| *Homo sapiens* | UDP glucuronosyltransferase | DQ383514.1 |
| *Mustela nigripes* | UDP glucuronosyltransferase-like | XM_059393759.1 |
| *Equus caballus* | UDP glucuronosyltransferase | XM_014740431.2 |
| *Propithecus coquereli* | UDP glucuronosyltransferase | XM_012648847.1 |
| *Marmota marmota marmota* | UDP glucuronosyltransferase | XM_048808769.1 |
| *Bubalus bubalis* | UDP glucuronosyltransferase | XM_025289186.2 |

In one aspect, the DNA constructs disclosed herein incorporate a gene that encodes 0-linked N-acetylglucosamine transferase (OGT). In a further aspect, OGT is an enzyme that catalyzes the addition of one N-acetylglucosamine involved in an O-glycosidic linkage to a serine or threonine. OGT may, in some aspects, compete for serine and threonine residues with protein kinases or may have substrate specificity. OGT is found in both cytoplasmic and mitochondrial isoforms.

In one aspect, the gene that encodes OGT is isolated from a mammal such as, for example, an Arctic ground squirrel, groundhog, yellow-bellied marmot, thirteen-lined ground squirrel, dromedary camel, carabao, Eastern gray squirrel, wild yak, domestic water buffalo, alpaca, hybrid cattle, cattle, brown bear, Bactrian camel, polar bear, olive baboon, gelada, sooty mangabey, American black bear, Etruscan shrew, drill, red deer, elk, giant panda, Tibetan macaque, striped hyena, Damara mole rat, siamang, crab-eating macaque, Indochinese rhesus macaque, cougar, horse, dog, clouded leopard, takin, Southern pig-tailed macaque, dingo, golden snub-nosed monkey, Angola colobus, goat, dwarf musk deer, common raccoon dog, bobcat, leopard cat, sheep, scimitar oryx, Canada lynx, red fox, white-tailed deer, cheetah, European rabbit, snow leopard, fishing cat, plains zebra, cat, common degu, green monkey, Alpine marmot, silvery gibbon, Bornean orangutan, common marmoset, or leopard. In a further aspect, the gene that encodes OGT has SEQ ID NO. 4 or at least 70% homology thereto, at least 75% homology thereto, at least 80% homology thereto, at least 85% homology thereto, at least 90% homology thereto, at least 95% homology thereto, or at least 99% homology thereto.

Other sequences encoding OGT or related or homologous genes can be identified in a database such as, for example, GenBank. In one aspect, the gene that encodes O-linked N-acetylglucosamine transferase (OGT) is isolated from *Urocitellus parryii* and can be identified by the GI number XM_026412627.1 in the GenBank database. In another aspect, sequences useful herein include those with GI numbers listed in Table 3:

TABLE 3

| O-Linked N-Acetylglucosamine Transferase | | |
|---|---|---|
| Source Organism | Sequence Description | GI Number |
| *Urocitellus parryii* | O-linked N-acetylglucosamine transferase | XM_026412627.1 |
| *Marmota monax* | O-linked N-acetylglucosamine transferase | XM_046467038.2 |
| *Marmota flaviventris* | O-linked N-acetylglucosamine transferase | XM_027935771.2 |
| *Ictidomys tridecemlineatus* | O-linked N-acetylglucosamine transferase | XM_021719915.2 |
| *Ictidomys tridecemlineatus* | O-linked N-acetylglucosamine transferase | XM_005339941.3 |
| *Urocitellus parryii* | O-linked N-acetylglucosamine transferase | XM_026412628.1 |
| *Camelus dromedarius* | O-linked N-acetylglucosamine transferase | XM_010978763.2 |
| *Marmota monax* | O-linked N-acetylglucosamine transferase | XM_046467039.2 |

TABLE 3-continued

| O-Linked N-Acetylglucosamine Transferase | | |
|---|---|---|
| Source Organism | Sequence Description | GI Number |
| *Bubalus carabanensis* | O-linked N-acetylglucosamine transferase | XM_055565162.1 |
| *Sciurus carolinensis* | O-linked N-acetylglucosamine transferase | XM_047535530.1 |
| *Marmota flaviventris* | O-linked N-acetylglucosamine transferase | XM_027935772.2 |
| *Bos mutus* | O-linked N-acetylglucosamine transferase | XM_005900810.2 |
| *Ictidomys tridecemlineatus* | O-linked N-acetylglucosamine transferase | XM_040281958.1 |
| *Ictidomys tridecemlineatus* | O-linked N-acetylglucosamine transferase | XM_005339942.3 |
| *Bubalus bubalis* | O-linked N-acetylglucosamine transferase | NM_001290907.1 |
| *Vicugna pacos* | O-linked N-acetylglucosamine transferase | XM_015250691.2 |
| *Bos indicus* × *Bos taurus* | O-linked N-acetylglucosamine transferase | XM_027534857.1 |
| *Bos taurus* | O-linked N-acetylglucosamine transferase | XM_005228027.5 |
| *Ursus arctos* | O-linked N-acetylglucosamine transferase | XM_026485785.4 |
| *Camelus bactrianus* | O-linked N-acetylglucosamine transferase | XM_010973595.2 |
| *Camelus bactrianus* | O-linked N-acetylglucosamine transferase | XM_045509212.1 |
| *Ursus maritimus* | O-linked N-acetylglucosamine transferase | XM_040630913.1 |
| *Bubalus carabanensis* | O-linked N-acetylglucosamine transferase | XM_055565164.1 |
| *Papio anubis* | O-linked N-acetylglucosamine transferase | XM_003917862.4 |
| *Theropithecus gelada* | O-linked N-acetylglucosamine transferase | XM_025371879.1 |
| *Cercocebus atys* | O-linked N-acetylglucosamine transferase | XM_012060760.1 |
| *Ursus americanus* | O-linked N-acetylglucosamine transferase | XM_045788783.1 |
| *Marmota flaviventris* | UDP-N-acetylglucosamine transferase | XM_034635621.1 |
| *Suncus etruscus* | O-linked N-acetylglucosamine transferase | XM_049767163.1 |
| *Mandrillus leucophaeus* | O-linked N-acetylglucosamine transferase | XM_011992070.1 |
| *Cervus elaphus* | O-linked N-acetylglucosamine transferase | XM_043897812.1 |
| *Cervus canadensis* | O-linked N-acetylglucosamine transferase | XM_043458227.1 |
| *Marmota monax* | UDP-N-acetylglucosamine transferase | XM_046468327.2 |
| *Ailuropoda melanoleuca* | O-linked N-acetylglucosamine transferase | XM_002930577.4 |
| *Camelus dromedarius* | O-linked N-acetylglucosamine transferase | XM_010978764.2 |
| *Bubalus carabanensis* | O-linked N-acetylglucosamine transferase | XM_055565163.1 |
| *Macaca thibetana thibetana* | O-linked N-acetylglucosamine transferase | XM_050776310.1 |
| *Sciurus carolinensis* | O-linked N-acetylglucosamine transferase | XM_047535531.1 |
| *Bubalus bubalis* | O-linked N-acetylglucosamine transferase | XM_006050820.3 |
| *Hyaena hyaena* | O-linked N-acetylglucosamine transferase | XM_039253321.1 |
| *Fukomys damarensis* | O-linked N-acetylglucosamine transferase | XM_010607954.3 |
| *Symphalangus syndactylus* | O-linked N-acetylglucosamine transferase | XM_055268542.1 |
| *Bos mutus* | O-linked N-acetylglucosamine transferase | XM_005900811.2 |
| *Macaca fascicularis* | O-linked N-acetylglucosamine transferase | XM_005593919.2 |
| *Vicugna pacos* | O-linked N-acetylglucosamine transferase | XM_015250692.2 |
| *Macaca mulatta* | O-linked N-acetylglucosamine transferase | XM_015127666.2 |
| *Bos indicus* × *Bos taurus* | O-linked N-acetylglucosamine transferase | XM_027534858.1 |
| *Puma concolor* | O-linked N-acetylglucosamine transferase | XM_025933892.1 |
| *Equus caballus* | O-linked N-acetylglucosamine transferase | XM_001493372.5 |
| *Canis lupus familiaris* | O-linked N-acetylglucosamine transferase | XM_844299.5 |
| *Neofelis nebulosa* | O-linked N-acetylglucosamine transferase | XM_058714361.1 |
| *Ursus arctos* | O-linked N-acetylglucosamine transferase | XM_026485786.4 |
| *Budorcas taxicolor* | O-linked N-acetylglucosamine transferase | XM_052663930.1 |
| *Macaca nemestrina* | O-linked N-acetylglucosamine transferase | XM_011732741.1 |
| *Canis lupus dingo* | O-linked N-acetylglucosamine transferase | XM_025466166.3 |
| *Camelus bactrianus* | O-linked N-acetylglucosamine transferase | XM_010973596.2 |
| *Ursus maritimus* | O-linked N-acetylglucosamine transferase | XM_040630922.1 |
| *Bos taurus* | O-linked N-acetylglucosamine transferase | NM_001098070.2 |
| *Bos taurus* | UDP-N-acetylglucosamine transferase | BC140542.1 |
| *Rhinopithecus roxellana* | O-linked N-acetylglucosamine transferase | XM_010366585.2 |
| *Colobus angolensis palliatus* | O-linked N-acetylglucosamine transferase | XM_011943084.1 |
| *Papio anubis* | O-linked N-acetylglucosamine transferase | XM_003917863.5 |
| *Theropithecus gelada* | O-linked N-acetylglucosamine transferase | XM_025371880.1 |
| *Capra hircus* | O-linked N-acetylglucosamine transferase | XM_013976396.2 |
| *Moschus berezovskii* | O-linked N-acetylglucosamine transferase | XM_055437763.1 |
| *Nyctereutes procyonoides* | O-linked N-acetylglucosamine transferase | XM_055337680.1 |
| *Cercocebus atys* | O-linked N-acetylglucosamine transferase | XM_012060761.1 |
| *Lynx rufus* | O-linked N-acetylglucosamine transferase | XM_047092606.1 |
| *Ursus americanus* | O-linked N-acetylglucosamine transferase | XM_045788784.1 |
| *Prionailurus bengalensis* | O-linked N-acetylglucosamine transferase | XM_043570677.1 |
| *Ovis aries* | O-linked N-acetylglucosamine transferase | XM_004022178.5 |
| *Oryx dammah* | O-linked N-acetylglucosamine transferase | XM_040265706.1 |
| *Canis lupus familiaris* | O-linked N-acetylglucosamine transferase | XM_038587694.1 |
| *Canis lupus familiaris* | O-linked N-acetylglucosamine transferase | XM_038450274.1 |
| *Suncus etruscus* | O-linked N-acetylglucosamine transferase | XM_049767164.1 |
| *Lynx canadensis* | O-linked N-acetylglucosamine transferase | XM_030306277.2 |
| *Vulpes vulpes* | O-linked N-acetylglucosamine transferase | XM_025982889.1 |
| *Odocoileus virginianus texanus* | O-linked N-acetylglucosamine transferase | XM_020882917.1 |
| *Odocoileus virginianus texanus* | O-linked N-acetylglucosamine transferase | XM_020882916.1 |
| *Acinonyx jubatus* | O-linked N-acetylglucosamine transferase | XM_053202468.1 |
| *Oryctolagus cuniculus* | O-linked N-acetylglucosamine transferase | XM_002720103.4 |
| *Mandrillus leucophaeus* | O-linked N-acetylglucosamine transferase | XM_011992071.1 |
| *Panthera uncia* | O-linked N-acetylglucosamine transferase | XM_049643946.1 |
| *Prionailurus viverrinus* | O-linked N-acetylglucosamine transferase | XM_047843412.1 |

TABLE 3-continued

| O-Linked N-Acetylglucosamine Transferase | | |
|---|---|---|
| Source Organism | Sequence Description | GI Number |
| *Equus quagga* | O-linked N-acetylglucosamine transferase | XM_046672660.1 |
| *Equus quagga* | O-linked N-acetylglucosamine transferase | XM_046672658.1 |
| *Felis catus* | O-linked N-acetylglucosamine transferase | XM_004000621.6 |
| *Cervus elaphus* | O-linked N-acetylglucosamine transferase | XM_043897813.1 |
| *Cervus canadensis* | O-linked N-acetylglucosamine transferase | XM_043458228.1 |
| *Octodon degus* | O-linked N-acetylglucosamine transferase | XM_004646785.1 |
| *Chlorocebus sabaeus* | O-linked N-acetylglucosamine transferase | XM_007992035.2 |
| *Marmota marmota marmota* | O-linked N-acetylglucosamine transferase | XM_048797676.1 |
| *Panthera uncia* | O-linked N-acetylglucosamine transferase | XM_049643948.1 |
| *Ailuropoda melanoleuca* | O-linked N-acetylglucosamine transferase | XM_002930576.4 |
| *Hylobates moloch* | O-linked N-acetylglucosamine transferase | XM_032757158.2 |
| *Pongo pygmaeus* | O-linked N-acetylglucosamine transferase | XM_054470805.1 |
| *Callithrix jacchus* | O-linked N-acetylglucosamine transferase | XM_002762977.4 |
| *Panthera pardus* | O-linked N-acetylglucosamine transferase | XM_019428710.2 |
| *Macaca thibetana thibetana* | O-linked N-acetylglucosamine transferase | XM_050776312.1 |
| *Hyaena hyaena* | O-linked N-acetylglucosamine transferase | XM_039253324.1 |

In one aspect, the DNA constructs disclosed herein incorporate a gene that encodes alcohol dehydrogenase, such as, for example, alcohol dehydrogenase II (ADHII). In one aspect, the gene that expresses alcohol dehydrogenase catalyzes the conversion of ethanol to acetaldehyde. In another aspect, alcohol dehydrogenase can act with any one of a number of primary unbranched aliphatic alcohols. In some aspects, alcohol dehydrogenase II requires at least two $Zn^{2+}$ ions per subunit to function. In other aspects, one molecule of $NAD^+$ is required to convert an alcohol to an aldehyde or ketone using alcohol dehydrogenase.

In one aspect, the gene that encodes alcohol dehydrogenase is isolated from a fungus such as, for example, a *Saccharomyces cerevisiae* strain including, but not limited to, N85, S288C, YJM1083, YJM1129, YJM1133, YJM1190, YJM1208, YJM1244, YJM1250, YJM1252, YJM1307, YJM1336, YJM1356, YJM1381, YJM1383, YJM1385, YJM1386, YJM1387, YJM1388, YJM1389, YJM1415, YJM1417, YJM1419, YJM1433, YJM1460, YJM1478, YJM1526, YJM1527, YJM1592, YJM1615, YJM271, YJM450, YJM451, YJM453, YJM456, YJM470, YJM541, YJM554, YJM555, YJM681, YJM682, YJM689, YJM969, YJM972, YJM975, YJM978, YJM981, YJM984, YJM987, YJM990, YJM993, or YJM996. In a further aspect, the gene that encodes alcohol dehydrogenase has SEQ ID NO. 3 or at least 70% homology thereto, at least 75% homology thereto, at least 80% homology thereto, at least 85% homology thereto, at least 90% homology thereto, at least 95% homology thereto, or at least 99% homology thereto.

Other sequences encoding alcohol dehydrogenase or related or homologous genes can be identified in a database such as, for example, GenBank. In one aspect, the gene that encodes alcohol dehydrogenase is isolated from *Saccharomyces cerevisiae* and can be identified by the GI number CP033482.1 in the GenBank database. In another aspect, sequences useful herein include those with GI numbers listed in Table 4:

TABLE 4

| Alcohol Dehydrogenase | | |
|---|---|---|
| Source Organism | Sequence Description | GI Number |
| *Saccharomyces cerevisiae* | Genomic DNA | CP033482.1 |
| *Saccharomyces cerevisiae* | Genomic DNA | CP033499.1 |
| *Saccharomyces cerevisiae* | Genomic DNA | CP029160.1 |
| *Saccharomyces cerevisiae* | Genomic DNA | CP026291.1 |
| *Saccharomyces cerevisiae* | Genomic DNA | CP020135.1 |
| *Saccharomyces cerevisiae* YJM1386 | Genomic DNA | CP005453.2 |
| *Saccharomyces cerevisiae* YJM1385 | Genomic DNA | CP005452.2 |
| *Saccharomyces cerevisiae* YJM1381 | Genomic DNA | CP005450.2 |
| *Saccharomyces cerevisiae* | Genomic DNA | AP026844.1 |
| *Saccharomyces cerevisiae* | Genomic DNA | CP089112.1 |
| *Saccharomyces cerevisiae* | Genomic DNA | CP059534.2 |
| *Saccharomyces cerevisiae* S288C | Genomic DNA | BK006946.2 |
| *Saccharomyces cerevisiae* S288C | Alcohol dehydrogenase II | NM_001182812.1 |
| *Saccharomyces cerevisiae* | Genomic DNA | Z49212.1 |
| synthetic construct | Genomic DNA | EF059086.1 |
| *Saccharomyces cerevisiae* | Alcohol dehydrogenase II | J01314.1 |
| *Saccharomyces cerevisiae* | Genomic DNA | CP046462.1 |
| *Saccharomyces cerevisiae* | Genomic DNA | CP072087.1 |
| *Saccharomyces cerevisiae* | Genomic DNA | CP072103.1 |
| *Saccharomyces cerevisiae* | Alcohol dehydrogenase | M38457.1 |
| *Saccharomyces cerevisiae* | Genomic DNA | CP024007.1 |
| *Saccharomyces cerevisiae* | Genomic DNA | CP096547.1 |
| *Saccharomyces cerevisiae* YJM1419 | Genomic DNA | CP005464.2 |
| *Saccharomyces cerevisiae* YJM1615 | Genomic DNA | CP005483.2 |
| *Saccharomyces cerevisiae* YJM1208 | Genomic DNA | CP005432.2 |
| *Saccharomyces cerevisiae* | Genomic DNA | CP080615.1 |

TABLE 4-continued

| Alcohol Dehydrogenase | | |
|---|---|---|
| Source Organism | Sequence Description | GI Number |
| *Saccharomyces cerevisiae* YJM1592 | Genomic DNA | CP005482.2 |
| *Saccharomyces cerevisiae* N85 | Genomic DNA | LN907796.1 |
| *Saccharomyces cerevisiae* YJM1389 | Genomic DNA | CP005456.1 |
| *Saccharomyces cerevisiae* YJM1388 | Genomic DNA | CP005455.1 |
| *Saccharomyces cerevisiae* YJM1307 | Genomic DNA | CP005440.1 |
| *Saccharomyces cerevisiae* S288C | Genomic DNA | CP092959.1 |
| *Saccharomyces cerevisiae* | Genomic DNA | CP088322.1 |
| *Saccharomyces cerevisiae* | Genomic DNA | CP088313.1 |
| *Saccharomyces cerevisiae* | Alcohol dehydrogenase I | MH845639.1 |
| *Saccharomyces cerevisiae* | Genomic DNA | CP020203.1 |
| *Saccharomyces cerevisiae* YJM451 | Genomic DNA | CP005403.2 |
| *Saccharomyces cerevisiae* YJM1460 | Genomic DNA | CP005472.2 |
| *Saccharomyces cerevisiae* | Genomic DNA | CP093777.1 |
| *Saccharomyces cerevisiae* | Genomic DNA | CP036475.1 |
| *Saccharomyces cerevisiae* YJM1433 | Genomic DNA | CP005465.2 |
| *Saccharomyces cerevisiae* YJM456 | Genomic DNA | CP005405.2 |
| *Saccharomyces cerevisiae* YJM689 | Genomic DNA | CP005414.2 |
| *Saccharomyces cerevisiae* YJM682 | Genomic DNA | CP005412.2 |
| *Saccharomyces cerevisiae* YJM1383 | Genomic DNA | CP005451.2 |
| *Saccharomyces cerevisiae* | Genomic DNA | CP011559.1 |
| *Saccharomyces cerevisiae* | Genomic DNA | AP027356.1 |
| *Saccharomyces cerevisiae* YJM1250 | Genomic DNA | CP005436.1 |
| *Saccharomyces cerevisiae* YJM1083 | Genomic DNA | CP005426.1 |
| *Saccharomyces cerevisiae* YJM470 | Genomic DNA | CP005406.1 |
| *Saccharomyces cerevisiae* | Genomic DNA | CP093761.1 |
| *Saccharomyces cerevisiae* | Alcohol dehydrogenase II | JX901290.1 |
| *Saccharomyces cerevisiae* | Genomic DNA | CP025109.1 |
| *Saccharomyces cerevisiae* | Genomic DNA | CP020169.1 |
| *Saccharomyces cerevisiae* YJM1356 | Genomic DNA | CP005449.2 |
| *Saccharomyces cerevisiae* YJM1190 | Genomic DNA | CP005429.2 |
| *Saccharomyces cerevisiae* YJM978 | Genomic DNA | CP005419.2 |
| *Saccharomyces cerevisiae* YJM555 | Genomic DNA | CP005409.2 |
| *Saccharomyces cerevisiae* YJM1133 | Genomic DNA | CP005428.2 |
| *Saccharomyces cerevisiae* YJM975 | Genomic DNA | CP005418.2 |
| *Saccharomyces cerevisiae* YJM554 | Genomic DNA | CP005408.2 |
| *Saccharomyces cerevisiae* YJM1526 | Genomic DNA | CP005477.2 |
| *Saccharomyces cerevisiae* YJM972 | Genomic DNA | CP005417.2 |
| *Saccharomyces cerevisiae* YJM996 | Genomic DNA | CP005425.2 |
| *Saccharomyces cerevisiae* | Genomic DNA | CP008265.1 |
| *Saccharomyces cerevisiae* | Genomic DNA | CP008367.1 |
| *Saccharomyces cerevisiae* | Genomic DNA | CP008554.1 |
| *Saccharomyces cerevisiae* | Genomic DNA | CP008537.1 |
| *Saccharomyces cerevisiae* | Genomic DNA | CP008520.1 |
| *Saccharomyces cerevisiae* | Genomic DNA | CP008129.1 |
| *Saccharomyces cerevisiae* | Genomic DNA | CP007993.1 |
| *Saccharomyces cerevisiae* YJM1336 | Genomic DNA | CP005444.2 |
| *Saccharomyces cerevisiae* YJM1244 | Genomic DNA | CP005434.2 |
| *Saccharomyces cerevisiae* YJM993 | Genomic DNA | CP005424.2 |
| *Saccharomyces cerevisiae* YJM453 | Genomic DNA | CP005404.2 |
| *Saccharomyces cerevisiae* YJM990 | Genomic DNA | CP005423.2 |
| *Saccharomyces cerevisiae* YJM987 | Genomic DNA | CP005422.2 |
| *Saccharomyces cerevisiae* YJM450 | Genomic DNA | CP005402.2 |
| *Saccharomyces cerevisiae* YJM984 | Genomic DNA | CP005421.2 |
| *Saccharomyces cerevisiae* YJM681 | Genomic DNA | CP005411.2 |
| *Saccharomyces cerevisiae* YJM981 | Genomic DNA | CP005420.2 |
| *Saccharomyces cerevisiae* YJM1129 | Genomic DNA | CP005427.1 |
| *Saccharomyces cerevisiae* YJM969 | Genomic DNA | CP005416.1 |
| *Saccharomyces cerevisiae* | Genomic DNA | CP097144.1 |
| *Saccharomyces cerevisiae* | Genomic DNA | CP093825.1 |
| *Saccharomyces cerevisiae* | Genomic DNA | CP093697.1 |
| *Saccharomyces cerevisiae* | Genomic DNA | CP093681.1 |
| *Saccharomyces cerevisiae* | Genomic DNA | CP093585.1 |
| *Saccharomyces cerevisiae* | Glucose-repressible ADHII | KJ137141.1 |
| *Saccharomyces cerevisiae* | Genomic DNA | CP008010.1 |
| *Saccharomyces cerevisiae* YJM1478 | Genomic DNA | CP005475.2 |
| *Saccharomyces cerevisiae* | Genomic DNA | CP008503.1 |
| *Saccharomyces cerevisiae* | Genomic DNA | CP008401.1 |
| *Saccharomyces cerevisiae* YJM271 | Genomic DNA | CP005398.2 |
| *Saccharomyces cerevisiae* YJM1527 | Genomic DNA | CP005478.2 |
| *Saccharomyces cerevisiae* YJM1252 | Genomic DNA | CP005437.2 |
| *Saccharomyces cerevisiae* YJM541 | Genomic DNA | CP005407.2 |
| *Saccharomyces cerevisiae* YJM1387 | Genomic DNA | CP005454.2 |
| *Saccharomyces cerevisiae* YJM1417 | Genomic DNA | CP005462.2 |
| *Saccharomyces cerevisiae* YJM1415 | Genomic DNA | CP005461.2 |

In one aspect, the DNA constructs disclosed herein incorporate a gene that encodes cytochrome P450. In a further aspect, cytochrome P450 is an enzyme that oxidizes steroids, fatty acids, and external compounds such as drugs. In an aspect, cytochrome P450 is involved in the clearance of certain drugs from the body. Cytochrome P450 enzymes typically include a heme-iron center which is used in catalysis.

In one aspect, the gene that encodes cytochrome P450 is isolated from a mammal such as, for example, a human, bonobo, chimpanzee, Western lowland gorilla, siamang, Northern white-cheeked gibbon, olive baboon, Sumatran orangutan, grivet, gelada, Bornean orangutan, Indochinese rhesus macaque, Japanese macaque, green monkey, Angola colobus, Southern pig-tailed macaque, Tibetan macaque, sooty mangabey, drill, crab-eating macaque, golden snub-nosed monkey, Francois' langur, Ugandan red colobus, tufted capuchin, black-and-white snub-nosed monkey, Panamanian white-faced capuchin, black-capped squirrel monkey, common marmoset, Nancy Ma's night monkey, or silvery gibbon. In a further aspect, the gene that encodes cytochrome P450 has SEQ ID NO. 5 or at least 70% homology thereto, at least 75% homology thereto, at least 80% homology thereto, at least 85% homology thereto, at least 90% homology thereto, at least 95% homology thereto, or at least 99% homology thereto.

Other sequences encoding cytochrome P450 or related or homologous genes can be identified in a database such as, for example, GenBank. In one aspect, the gene that encodes cytochrome P450 family 3 subfamily A member 4 is isolated from *Homo sapiens* and can be identified by the GI number DQ924960.1 in the GenBank database. In another aspect, sequences useful herein include those with GI numbers listed in Table 5:

TABLE 5

| Cytochrome P450 Family 3 Subfamily A Member 4 | | |
|---|---|---|
| Source Organism | Sequence Description | GI Number |
| *Homo sapiens* | Cytochrome P450 3A4 | DQ924960.1 |
| *Homo sapiens* | Cytochrome P450 3A4 | NM_001202855.3 |
| *Homo sapiens* | Cytochrome P450 3A4 | NM_017460.6 |
| *Homo sapiens* | Cytochrome P450 3A4 | AK312967.1 |
| *Homo sapiens* | Synthetic construct | BC069352.1 |
| *Homo sapiens* | Cytochrome P450 3A4 | BC101631.1 |
| *Homo sapiens* | Cytochrome P450 3A4 | BC069418.1 |
| *Homo sapiens* | Nifedipine oxidase | J04449.1 |
| *Homo sapiens* | Nifedipine oxidase | M18907.1 |
| *Human ORFeome Gateway entry vector* | Synthetic construct | LT739947.1 |
| synthetic construct | Cytochrome P450 3A4 | KJ891017.1 |
| *Homo sapiens* | Cytochrome P450 | X12387.1 |
| synthetic construct | Cytochrome P450 3A4 | KR711354.1 |
| synthetic construct | Cytochrome P450 3A4 | KR711353.1 |
| synthetic construct | Cytochrome P450 3A4 | KR711352.1 |
| synthetic construct | Cytochrome P450 3A4 | KR711351.1 |
| *Homo sapiens* | Nifedipine oxidase | M14096.1 |
| *Pan paniscus* | Cytochrome P450 3A4 | XM_057302722.1 |
| *Pan troglodytes* | Cytochrome P450 3A4 | NM_001122775.1 |
| *Homo sapiens* | Cytochrome P450 3A4 | AF182273.1 |
| *Homo sapiens* | Cytochrome P450 3A4 | AY606313.2 |
| *Homo sapiens* | Cytochrome P450 3A4 | AJ563375.1 |
| *Homo sapiens* | Cytochrome P450 | D00003.1 |
| *Gorilla gorilla gorilla* | Cytochrome P450 3A4 | XM_031013170.2 |
| *Symphalangus syndactylus* | Cytochrome P450 3A4 | XM_055292474.1 |
| *Symphalangus syndactylus* | Cytochrome P450 3A4 | XM_055292473.1 |
| *Nomascus leucogenys* | Cytochrome P450 3A4 | XM_012496486.2 |
| *Papio anubis* | Cytochrome P450 3A8 | XM_003895756.3 |
| *Pongo abelii* | Cytochrome P450 3A8 | XM_002817735.5 |
| *Nomascus leucogenys* | Cytochrome P450 3A4 | XM_030796958.1 |
| *Chlorocebus aethiops* | Cytochrome P450 3A4 | DQ022198.1 |
| *Theropithecus gelada* | Cytochrome P450 3A8 | XM_025380515.1 |
| *Pongo pygmaeus* | Cytochrome P450 3A8 | XM_054497199.1 |
| *Theropithecus gelada* | Cytochrome P450 3A8 | XM_025380518.1 |
| *Pongo pygmaeus* | Cytochrome P450 3A4 | EF589794.1 |
| *Chlorocebus aethiops* | Cytochrome P450 3A4 | DQ022197.1 |
| *Theropithecus gelada* | Cytochrome P450 3A8 | XM_025380517.1 |
| *Macaca mulatta* | Cytochrome P450 3A64 | AY334551.1 |
| *Macaca fuscata* | Cytochrome P450 3A | AB124894.1 |
| *Chlorocebus sabaeus* | Cytochrome P450 3A8 | XM_037990561.1 |
| *Colobus angolensis palliatus* | Cytochrome P450 3A8 | XM_011943841.1 |
| *Macaca nemestrina* | Cytochrome P450 3A8 | XM_011768405.1 |
| *Colobus angolensis palliatus* | Cytochrome P450 3A8 | XM_011943838.1 |
| *Macaca thibetana thibetana* | Cytochrome P450 3A8 | XR_007724181.1 |
| *Macaca thibetana thibetana* | Cytochrome P450 3A8 | XR_007724180.1 |
| *Macaca thibetana thibetana* | Cytochrome P450 3A8 | XR_007724179.1 |
| *Macaca thibetana thibetana* | Cytochrome P450 3A8 | XM_050784023.1 |
| *Macaca mulatta* | Cytochrome P450 3A64 | NM_001040414.1 |
| *Cercocebus atys* | Cytochrome P450 3A8 | XM_012057155.1 |
| *Mandrillus leucophaeus* | Cytochrome P450 3A8 | XM_011985743.1 |
| *Macaca fascicularis* | Cytochrome P450 3A4 | XM_045389498.1 |
| *Macaca fascicularis* | Cytochrome P450 3A | S53047.1 |
| *Mandrillus leucophaeus* | Cytochrome P450 3A8 | XM_011985742.1 |
| *Macaca thibetana thibetana* | Cytochrome P450 3A8 | XM_050784025.1 |

TABLE 5-continued

| Cytochrome P450 Family 3 Subfamily A Member 4 | | |
| --- | --- | --- |
| Source Organism | Sequence Description | GI Number |
| *Macaca thibetana thibetana* | Cytochrome P450 3A8 | XM_050784024.1 |
| *Colobus angolensis palliatus* | Cytochrome P450 3A8 | XM_011943842.1 |
| *Rhinopithecus roxellana* | Cytochrome P450 3A8 | XM_010377670.2 |
| *Macaca thibetana thibetana* | Cytochrome P450 3A8 | XM_050784026.1 |
| *Trachypithecus francoisi* | Cytochrome P450 3A8 | XM_033191867.1 |
| *Homo sapiens* | Cytochrome P450 | AJ563376.1 |
| *Piliocolobus tephrosceles* | Cytochrome P450 3A8 | XM_031935988.1 |
| *Mandrillus leucophaeus* | Cytochrome P450 3A8 | XM_011985744.1 |
| *Sapajus apella* | Cytochrome P450 3A21 | XM_032255266.1 |
| *Rhinopithecus bieti* | Cytochrome P450 3A8-like | XM_017886088.1 |
| *Trachypithecus francoisi* | Cytochrome P450 3A7 | XM_033191871.1 |
| *Cebus imitator* | Cytochrome P450 3A4 | XM_017533658.1 |
| *Saimiri boliviensis boliviensis* | Cytochrome P450 3A4 | XM_003934216.3 |
| *Saimiri boliviensis boliviensis* | Cytochrome P450 3A4 | DQ784117.1 |
| *Symphalangus syndactylus* | Cytochrome P450 3A7-like | XM_055292476.1 |
| *Callithrix jacchus* | Cytochrome P450 3A4 | KJ922565.1 |
| *Callithrix jacchus* | Cytochrome P450 3A4 | NM_001204440.1 |
| *Symphalangus syndactylus* | Cytochrome P450 3A7-like | XM_055292477.1 |
| *Symphalangus syndactylus* | Cytochrome P450 3A4 | XM_055292475.1 |
| *Chlorocebus sabaeus* | Cytochrome P450 3A166 | XM_008018620.2 |
| *Aotus nancymaae* | Cytochrome P450 3A21 | XM_012455547.2 |
| *Nomascus leucogenys* | Cytochrome P450 3A4 | XM_004090903.3 |
| *Mandrillus leucophaeus* | Cytochrome P450 3A8-like | XM_011985745.1 |
| *Papio anubis* | Cytochrome P450 3A7 | XM_009202655.4 |
| *Nomascus leucogenys* | Cytochrome P450 3A7 | XM_030796955.1 |
| *Nomascus leucogenys* | Cytochrome P450 3A7 | XM_030796954.1 |
| *Theropithecus gelada* | Cytochrome P450 3A7 | XM_025380525.1 |
| *Chlorocebus aethiops* | Cytochrome P450 3A7 | DQ022199.1 |
| *Chlorocebus sabaeus* | Cytochrome P450 3A166 | XM_037990554.1 |
| *Hylobates moloch* | Cytochrome P450 3A7 | XM_032756001.2 |
| *Symphalangus syndactylus* | Cytochrome P450 3A7 | XM_055292444.1 |
| *Symphalangus syndactylus* | Cytochrome P450 3A7 | XM_055292443.1 |
| *Cercocebus atys* | Cytochrome P450 3A7 | XM_012057149.1 |
| *Cercocebus atys* | Cytochrome P450 3A7 | XM_012057148.1 |
| *Pan troglodytes* | Cytochrome P450 3A67 | EF589799.1 |
| *Pongo abelii* | Cytochrome P450 3A7-like | XM_002817733.5 |
| *Pongo pygmaeus* | Cytochrome P450 3A7 | XM_054497200.1 |
| *Pongo pygmaeus* | Cytochrome P450 3A67 | EF589796.1 |
| *Pan paniscus* | Cytochrome P450 3A67 | XM_034964542.2 |
| *Papio anubis* | Cytochrome P450 3A7 | XM_003895757.5 |
| *Mandrillus leucophaeus* | Cytochrome P450 3A7 | XM_011985752.1 |
| *Macaca mulatta* | Cytochrome P450 3A7 | NM_001195758.2 |
| *Chlorocebus sabaeus* | Cytochrome P450 3A7 | XM_008018612.2 |
| *Macaca thibetana thibetana* | Cytochrome P450 3A7 | XM_050784027.1 |
| *Symphalangus syndactylus* | Cytochrome P450 3A7 | XM_055292446.1 |
| *Pan troglodytes* | Cytochrome P450 3A67 | NM_001093774.1 |

In one aspect, the DNA construct has the following genetic components: a) a gene that encodes a sulfotransferase, b) a gene that encodes UGT, c) a gene that encodes OGT, d) a gene that encodes an alcohol dehydrogenase, and e) a gene that encodes cytochrome P450 family 3 subfamily A member 4.

In another aspect, said construct further includes a) a promoter, b) a terminator or stop sequence, c) a gene that confers resistance to an antibiotic (a "selective marker"), d) a reporter protein, or any combination thereof. Each of these elements is described in further detail below.

In one aspect, the construct includes from 5' to 3' the following genetic components in the following order: (1) a gene that encodes sulfotransferase, (2) a gene that encodes UGT, (3) a gene that encodes OGT, (4) a gene that encodes an alcohol dehydrogenase, and (5) a gene that encodes cytochrome P450 family 3 subfamily A member 4.

In one aspect, the construct includes from 5' to 3' the following genetic components in the following order: a gene that encodes sulfotransferase having SEQ ID NO. 1 or at least 70% homology thereto, a gene that encodes UGT having SEQ ID NO. 2 or at least 70% homology thereto, a gene that encodes OGT having SEQ ID NO. 4 or at least 70% homology thereto, a gene that encodes an alcohol dehydrogenase having SEQ ID NO. 3 or at least 70% homology thereto, and a gene that encodes a cytochrome P450 having SEQ ID NO. 5 or at least 70% homology thereto. In some aspects, the construct optionally includes a gene that encodes enhanced green fluorescent protein having SEQ ID NO. 6 or at least 70% homology thereto.

In another aspect, the construct includes from 5' to 3' the following genetic components in the following order: (1) a gene that encodes sulfotransferase, (2) a CYC1 terminator, (3) a GAL1 promoter, (4) a gene that encodes UGT, (5) a CYC1 terminator, (6) a GAL1 promoter, (7) a gene that encodes OGT, (8) a CYC1 terminator, (9) a GAL1 promoter, (10) a gene that encodes alcohol dehydrogenase, (11) a CYC1 terminator, (12) a GAL1 promoter, and (13) a gene that encodes cytochrome P450.

In another aspect, the construct includes from 5' to 3' the following genetic components in the following order: (1) a gene that encodes sulfotransferase having SEQ ID NO. 1 or at least 90% homology thereto, (2) a CYC1 terminator, (3) a GAL1 promoter, (4) a gene that encodes UGT having SEQ ID NO. 2 or at least 90% homology thereto, (5) a CYC1 terminator, (6) a GAL1 promoter, (7) a gene that encodes OGT having SEQ ID NO. 4 or at least 90% homology thereto, (8) a CYC1 terminator, (9) a GAL1 promoter, (10) a gene that encodes alcohol dehydrogenase having SEQ ID NO. 3 or at least 90% homology thereto, (11) a CYC1 terminator, (12) a GAL1 promoter, and (13) a gene that encodes cytochrome P450 having SEQ ID NO. 5 or at least 90% homology thereto.

In still another aspect, the construct is a pYES2 plasmid having from 5' to 3' the following genetic components in the following order: (1) a gene that encodes sulfotransferase having SEQ ID NO. 1 or at least 70% homology thereto, (2) a CYC1 terminator, (3) a GAL1 promoter, (4) a gene that encodes UGT having SEQ ID NO. 2 or at least 70% homology thereto, (5) a CYC1 terminator, (6) a GAL1 promoter, (7) a gene that encodes OGT having SEQ ID NO. 4 or at least 70% homology thereto, (8) a CYC1 terminator, (9) a GAL1 promoter, (10) a gene that encodes alcohol dehydrogenase having SEQ ID NO. 3 or at least 70% homology thereto, (11) a CYC1 terminator, (12) a GAL1 promoter, and (13) a gene that encodes cytochrome P450 having SEQ ID NO. 5 or at least 70% homology thereto. In some embodiments, the construct further includes a gene that encodes enhanced green fluorescent protein having SEQ ID NO. 6 or at least 70% homology thereto, placed in a position 3' to the gene that encodes cytochrome P450.

In another aspect, the DNA construct has SEQ ID NO. 7 or at least 70% homology thereto, at least 75% homology thereto, at least 80% homology thereto, at least 85% homology thereto, at least 90% homology thereto, at least 95% homology thereto, or at least 99% homology thereto.

Additional Components of the DNA Constructs

In another aspect, said construct further includes a) a promoter, b) a terminator or stop sequence, c) a gene that confers resistance to an antibiotic (a "selective marker"), d) a reporter protein, or any combination thereof.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In another aspect, the coding sequence to be controlled is located 3' to the promoter. In still another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter also may be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, araBAD promoter, and GAL1 promoter. In a further aspect, the promoter is a native part of the vector used herein. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides from a ribosomal binding site.

In one aspect, the promoter is a GAL1 promoter. In another aspect, the GAL1 promoter is native to the plasmid used to create the vector. In another aspect, a GAL1 promoter is positioned before the gene that encodes sulfotransferase, the gene that encodes UGT, the gene that encodes OGT, the gene that encodes alcohol dehydrogenase, the gene that encodes cytochrome P450, or any combination thereof. In another aspect, the promoter is a GAL1 promoter obtained from or native to the pYES2 plasmid.

In one aspect, the regulatory sequence is an operon such as, for example, the LAC operon or LAC operator. As used herein, an "operon" is a segment of DNA containing a group of genes wherein the group is controlled by a single promoter. Genes included in an operon are all transcribed together. In a further aspect, the operon is a LAC operon and can be induced when lactose crosses the cell membrane of the biological device.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is an rrnB terminator obtained from or native to the pBAD plasmid. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

Further Components of the DNA Constructs and Methods for Making Thereof

In another aspect, the vector contains one or more ribosomal binding sites. As used herein, a "ribosomal binding site" or "rbs" is a sequence of nucleotides located 5' to the start codon of an mRNA that recruits a ribosome to initiate protein translation. In one aspect, the ribosomal binding site can be positioned before one or more or all genes in the DNA construct, or a before a subset of genes in a DNA construct.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BasBI, NotI, XhoI, XphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA at a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior insertion into the plasmid. In a further aspect, a DNA ligase enzyme can be used to assist in the ligation process.

In another aspect, the ligation mix may be incubated in an electromagnetic chamber. In one aspect, the incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and commercially available. Such vectors include, but are not limited to, pWLneo, pSV2cat, pOG44, pXT1, pSG, pSVK3, pBSK, pYES, pYES2, pBSKII, pET, pUC, pUC19, pBAD, and pETDuet-1 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copier per host cell and will contain selectable markers (such as genes for antibiotic resistance) to show the skilled artisan to select host eels that have been successfully transfected with the plasmids (for example, by growing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector, which confers antibiotic resistance, can survive. Optimally, only cells containing the vector to be expressed will be cultured, as this will result in the highest production efficiency of the desired gene products (e.g., peptides). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In certain aspects, the DNA construct can include a gene that encodes a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a green fluorescent protein and the gene that encodes the reporter protein has SEQ ID NO.

6 or at least 70% homology thereto. The amount of fluorescence that is produced can be correlated to the amount of DNA incorporated into the transfected cells. The fluorescence produced can be detected and quantified using techniques known in the art. For example, spectrofluorometers are typically used to measure fluorescence.

The DNA construct described herein can be part of a vector. In one aspect, the vector is a plasmid, a phagemid, a cosmid, a yeast artificial chromosome, a bacterial artificial chromosome, a virus, a phage, or a transposon.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

Cells and Biological Devices

A variety of different types of cells can be used in the methods described herein. In one aspect, the cells can be wild-type cells (i.e., not genetically-modified). In one aspect, the cells are from an animal such as, for example, a mammal, bird, fish, reptile, amphibian, or invertebrate. In another aspect, the cells are from a plant such as, for example, an agricultural crop, a decorative plant, a woody plant, a medicinal plant, or a combination thereof. In another aspect, the cells are from a multicellular fungus such as, for example, a mushroom, a mycorrhizal fungus, or a commercially-important mold.

In another aspect, the cells include a biological device. A "biological device" is formed when a microbial cell is transfected with a DNA construct. The biological devices are generally composed of microbial host cells, where the host cells are transformed (i.e., genetically-modified) with a DNA construct.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce an extract or composition that can remove metals and/or other contaminants from water or petroleum, such as, for example, those disclosed herein. "Heterologous" genes and proteins are genes and proteins that have been experimentally inserted into a cell that are not normally expressed by the cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which an exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

Cell Culture

A satisfactory microbiological culture contains available sources of hydrogen donors and acceptors, carbon, nitrogen, sulfur, phosphorus, inorganic salts and, in certain cases, vitamins or other growth-promoting substances. For example, the addition of peptone provides a readily-available source of nitrogen and carbon. Furthermore, the use of different types of media results in different growth rates and different stationary phase densities. A rich media results in a short doubling time and higher cell density at stationary phase. Minimal media results in slow growth and low final cell densities. Efficient agitation and aeration increase final cell densities.

Culturing or fermenting of host cells can be accomplished by any technique known in the art. In one aspect, batch fermentation can be conducted. In batch fermentation, the composition of the culture medium is set at the beginning and the system is closed to future alterations. In some aspects, a limited form of batch fermentation may be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial cells are immobilized on a substrate. Fermentation may be carried out on any scale and may include methods in which literal "fermentation" is carried out as well as other culture methods that are non-fermentative.

In one aspect, the microorganisms can be cultured for a period of from 2 days to 2 weeks, or for about 2, about 3, about 4, about 5, about 6, about 7, about 8, about 9, about 10, about 11, about 12, about 13, or about 14 days, where any value can be the lower or upper endpoint of a range (e.g., about 3 days to about 13 days, about 8 days to about 12 days, etc.). In one aspect, the microorganisms are cultured for about 10 days.

In another aspect, the microorganisms can be cultured at any temperature appropriate for the microorganisms, with the understanding that the temperature may vary according to the microorganism (for example, a thermophilic microorganism may require a higher culture temperature than a mesophile). In one aspect, the microorganisms are cultured at a temperature of from about 20 to about 37° C., or are cultured at about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., or about 37° C., where any value can be the lower or upper endpoint of a range, where any value can be the lower or upper endpoint of a range (e.g., about 21° C. to about 36° C., about 25° C. to about 30° C., etc.).

In certain aspects, after culturing the microorganisms for a sufficient time, the microbial cells can be lysed with one or more enzymes. For example, when the microbial cells are fungal, the fungal cells can be lysed with lyticase. In one aspect, the lyticase concentration can be about 500 μL, about 600 μL, about 700 μL, about 800 μL, about 900 μL, or about 1,000 μL per liter of culture, where any value can be the lower or upper endpoint of a range, where any value can be the lower or upper endpoint of a range (e.g., about 500 μL to about 900 μL, about 600 μL to about 800 μL, etc.).

In addition to or in place of enzymes, other components can be used to facilitate lysis of the microbial cells. In one aspect, chitosan can be used in combination with an enzyme to lyse the microbial cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation. In one aspect, the chitosan is from about 60% to about 100% acetylated, or about 70%, about 75%, about 80%, about 85%, about 90%, about 95%, or about 100% acetylated, where any value can be the lower or upper endpoint of a range, where any value can be the lower or upper endpoint of a range (e.g., about 60% to about 90%, about 70% to about 80%, etc.).

The molecular weight of the chitosan can vary, as well. For example, the chitosan can comprise about 3, 4, 5, 6, 7, 8, 9, 10, 11, 12, 13, 14, 15, 16, 17, 18, 19, or 20 glucosamine units and/or N-acetylglucosamine units, where any value can be the lower or upper endpoint of a range, where any value can be the lower or upper endpoint of a range (e.g., 2 to 19, 3 to 10, 5 to 7, etc.). In one aspect, chitosan can be added until a concentration of about 0.0015%, about 0.0025%, about 0.005%, about 0.0075%, about 0.01%, about 0.015%, about 0.02%, about 0.03%, about 0.04%, or about 0.05%, where any value can be an upper or lower endpoint of a range (e.g., 0.002% to 0.04%, 0.05% to 0.015%, etc.).

In another aspect, cells can first be fermented, for example, in a biofermenter, at a temperature conducive to cell growth. In one aspect, the cells are fermented at 30° C. In a further aspect, the cells are fermented for a time period sufficient to produce the metabolite(s) of interest. In one aspect, the cells are fermented for from 6 hours to 96 hours, or for 6, 12, 18, 24, 30, 36, 42, 48, 54, 60, 66, 72, 78, 84, 90, or about 96 hours, or a combination of any of the foregoing values, or a range encompassing any of the foregoing values. In one aspect, during fermentation, a micro-current can be applied to the cells as described above. In some aspects, the micro-current is applied for the entire culture period. In another aspect, the micro-current is applied for only a part of the culture period, or for several non-consecutive parts of the culture period. In one aspect, the micro-current is the same throughout the entire culture period. In an alternative aspect, the micro-current is varied during the culture period.

Exemplary methods for culturing cells and/or the biological devices disclosed herein are provided in the Examples.

Culture Medium

In some aspects, the cells are suspended in a culture medium. In another aspect, the culture medium can be Dulbecco's Modified Eagle Medium (DMEM), RPMI 1640, Minimal Essential Medium (MEM), Eagle's Minimal Essential Medium (EMEM), Iscove's Modified Dulbecco's Medium (IMDM), DMEM/F12 Medium, Murashige and Skoog (MS) medium, White's medium, *Agrobacterium* minimal medium, Banana AGS basal medium, Blaydes basal medium, Bold's basal medium, Chu (N6) medium, De Greef and Jacobs Medium, DKW basal medium, Economou and Read basal medium, Gamborg (B5) medium, Gresshoff and Doy medium, Heller medium, Hoagland complete medium, Jensen's medium, Kao and Michayluk medium, Litvay medium, NB basal medium, Nitsch medium. NLN medium, Quoirin and Lepoivre medium, Schenk and Hildebrandt medium, TAP medium, TM4G medium, Vacin and Went medium, wheat callus induction medium, Luria Bertani (LB) broth, terrific broth, tryptic soy broth, minimal salts (M9) medium, SOB medium, SOC medium, yeast malt medium, YPD broth, YNB broth, synthetic complete (SC) medium, YPG medium, Hartwell's complete (HC) medium, or a combination thereof. In one aspect, the culture medium is Luria Bertani (LB) broth or yeast malt medium.

In another aspect, the culture medium can contain supplemental compounds such as, for example, vitamins, nucleosides, nucleotides, amino acids, a carbohydrate, an antibiotic, or a combination thereof.

In one aspect, the culture medium can be a liquid. In another aspect, the methods disclosed herein can be performed in a biofermenter. In an alternative aspect, the cells can be distributed on a substrate. In one aspect, the substrate can be agar, a culture dish, contaminated soil, a wastewater treatment device, mineral ore, a plant organ, a tissue scaffold, or a fermentable material. When the substrate is a plant organ, in some aspects, the plant organ can be a root, leaf, stem, rhizome, tuber, flower, seed, fruit, vegetable, callus, or a combination thereof. When the substrate is a fermentable material, in some aspects, the substrate can be milk, a grain, cabbage, soybeans, fish, or a biomass feedstock. When the substrate is a biomass feedstock, in some aspects, the substrate can be forestry residue, logging residue, sawmill residue, animal manure, a recycled material, a carbohydrate waste, corn cob, corn stover, wheat straw, nut hulls, soy hulls, switchgrass, gammagrass, paper, or a combination thereof.

Extraction and Purification of Metabolites

In one aspect, the methods disclosed herein can be used to increase the production of metabolites by cells. In some aspects, the metabolites are secreted into a culture medium and collected. In other aspects, the metabolites remain in the cells, requiring the cells to be lysed prior to collection and purification of the metabolites.

In one aspect, prior to collection of any metabolite(s) of interest, fermentation can be stopped. In some aspects, the micro-current will be withdrawn or turned off (e.g., by turning off a power supply to a biofermenter or a similar mechanism). In another aspect, an enzyme such as, for example, lyticase can optionally be used to lyse cells following fermentation. In still another aspect, the cell culture can optionally be autoclaved for a sufficient time following cell lysis in order to ensure no living cells remain in the culture. Following lysis and autoclaving, or instead of performing these two processes, centrifugation, sonication, and filtration can be performed to facilitate collection of relevant metabolites. In an alternative aspect, culture medium including an increased concentration of the desired metabolite(s) from the biofermenter can be used without further processing.

In any of the above aspects, cell cultures of biological devices such as those disclosed herein, purified metabolites, and/or extracts containing metabolites can be applied to other cells and/or tissues in order to increase metabolite production. In one aspect, the cell cultures, metabolites, and/or extracts are applied to plant tissue such as, for example, plant calluses. Following plant tissue growth, calluses can be crushed and macerated with a solvent in order to extract metabolites from the plant tissue. In one aspect, choice of solvent depends on the chemical characteristics of the metabolite being extracted. For example, lycopene would be extracted with a hydrophobic solvent.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

ASPECTS

The present disclosure can be described in accordance with the following numbered aspects, which should not be confused with the claims.

Aspect 1. A DNA construct comprising the following genetic components:

(a) a gene that encodes a sulfotransferase;

(b) a gene that encodes a UDP-glucuronosyltransferase (UGT);

(c) a gene that encodes an O-linked N-acetylglucosamine transferase (OGT);

(d) a gene that encodes an alcohol dehydrogenase; and (e) a gene that encodes a cytochrome P450.

Aspect 2. The DNA construct of aspect 1, wherein the gene that encodes the sulfotransferase has SEQ ID NO. 1 or at least 70% homology thereto.

Aspect 3. The DNA construct of aspect 1, wherein the gene that encodes the UGT has SEQ ID NO. 2 or at least 70% homology thereto.

Aspect 4. The DNA construct of aspect 1, wherein the gene that encodes the OGT has SEQ ID NO. 3 or at least 70% homology thereto.

Aspect 5. The DNA construct of aspect 1, wherein the gene that encodes the alcohol dehydrogenase has SEQ ID NO. 4 or at least 70% homology thereto.

Aspect 6. The DNA construct of aspect 1, wherein the gene that encodes the cytochrome P450 has SEQ ID NO. 5 or at least 70% homology thereto.

Aspect 7. The DNA construct of aspect 1, wherein the construct further comprises at least one promoter.

Aspect 8. The DNA construct of aspect 7, wherein the at least one promoter is a T3 promoter, a T7 promoter, an iron promoter, a GAL1 promoter, or any combination thereof.

Aspect 9. The DNA construct of aspect 8, wherein the at least one promoter is a GAL1 promoter, and the GAL1 promoter is positioned before the gene that encodes the sulfotransferase, UGT, OGT, alcohol dehydrogenase, cytochrome P450, or any combination thereof.

Aspect 10. The DNA construct of aspect 1, wherein the DNA construct further comprises a gene that confers resistance to an antibiotic.

Aspect 11. The DNA construct of aspect 10, wherein the antibiotic comprises tetracycline, neomycin, kanamycin, ampicillin, hygromycin, chloramphenicol, amphotericin B, bacitracin, carbapenem, cephalosporin, ethambutol, fluoroquinolones, isoniazid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

Aspect 12. The DNA construct of aspect 1, wherein the DNA construct further comprises at least one terminator.

Aspect 13. The DNA construct of aspect 12, wherein the at least one terminator is a CYC1 terminator.

Aspect 14. The DNA construct of aspect 1, wherein the DNA construct further comprises a reporter protein.

Aspect 15. The DNA construct of aspect 14, wherein the reporter protein is a fluorescent reporter protein.

Aspect 16. The DNA construct of aspect 15, wherein the fluorescent reporter protein is a red fluorescent protein, a cyan fluorescent protein, a green fluorescent protein, or a yellow fluorescent protein.

Aspect 17. The DNA construct of aspect 16, wherein the fluorescent reporter protein is a green fluorescent protein.

Aspect 18. The DNA construct of aspect 17, wherein the green fluorescent protein is SEQ ID NO. 6 or has at least 70% homology thereto.

Aspect 19. The DNA construct of aspect 1, wherein the construct comprises from 5' to 3' the following genetic components in the following order: (a) the gene that encodes the sulfotransferase; (b) the gene that encodes the UGT; (c) the gene that encodes the OGT; (d) the gene that encodes the alcohol dehydrogenase; and (e) the gene that encodes the cytochrome P450.

Aspect 20. The DNA construct of aspect 1, wherein the construct comprises from 5' to 3' the following genetic components in the following order: (a) the gene that encodes the sulfotransferase having SEQ ID NO. 1 or at least 70% homology thereto; (b) the gene that encodes the UGT having SEQ ID NO. 2 or at least 70% homology thereto; (c) the gene that encodes the OGT having SEQ ID NO. 3 or at least 70% homology thereto; (d) the gene that encodes the alcohol dehydrogenase having SEQ ID NO. 4 or at least 70% homology thereto; and (e) the gene that encodes the cytochrome P450 having SEQ ID NO. 5 of at least 70% homology thereto.

Aspect 21. The DNA construct of aspect 1, wherein the construct comprises from 5' to 3' the following genetic components in the following order: (a) the gene that encodes the sulfotransferase; (b) a CYC1 terminator; (c) a GAL1 promoter; (d) the gene that encodes the UGT; (e) a CYC1 terminator; (f) a GAL1 promoter; (g) the gene that encodes the OGT; (h) a CYC1 terminator; (i) a GAL1 promoter; (j) the gene that encodes the alcohol dehydrogenase; (k) a CYC1 terminator; (l) a GAL1 promoter; and (m) the gene that encodes the cytochrome P450.

Aspect 22. The DNA construct of aspect 1, wherein the construct comprises from 5' to 3' the following genetic components in the following order: (a) the gene that encodes the sulfotransferase having SEQ ID NO. 1 or at least 70% homology thereto; (b) a CYC1 terminator; (c) a GAL1 promoter; (d) the gene that encodes the UGT having SEQ ID NO. 2 or at least 70% homology thereto; (e) a CYC1 terminator; (f) a GAL1 promoter; (g) the gene that encodes the OGT having SEQ ID NO. 3 or at least 70% homology thereto; (h) a CYC1 terminator; (i) a GAL1 promoter; (j) the gene that encodes the alcohol dehydrogenase having SEQ ID NO. 4 or at least 70% homology thereto; (k) a CYC1 terminator; (l) a GAL1 promoter; and (m) the gene that encodes the cytochrome P450 having SEQ ID NO. 5 or at least 70% homology thereto.

Aspect 23. The DNA construct of aspect 1, wherein the DNA construct has SEQ ID NO. 7.

Aspect 24. A vector comprising the DNA construct of aspect 1.

Aspect 25. The vector of aspect 24, wherein the vector is a plasmid.

Aspect 26. The vector of aspect 25, wherein the plasmid is pWLneo, pSV2cat, pOG44, pXT1, pSG, pSVK3, pBSK, pBSKII, pYES, pYES2, pET, pUC, or pUC19.

Aspect 27. The vector of aspect 26, wherein the vector is pYES2.

Aspect 28. A biological device comprising host cells transformed with the DNA construct in any one of aspects 1-23.

Aspect 29. The device of aspect 28, wherein the host cells comprise fungi or bacteria.

Aspect 30. The device of aspect 29, wherein the fungi comprise *Saccharomyces cerevisiae.*

Aspect 31. A method for producing a composition for detecting or detoxifying alcohol or opioids, the method comprising growing the biological device of any one of aspects 28-30 for a time sufficient to produce the composition.

Aspect 32. The method of aspect 31, wherein after growing the biological device to produce the composition, the method further comprises the step of lysing the host cells in the composition to produce a lysed composition.

Aspect 33. A composition produced by the method of aspect 31 or 32.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: Preparation of DNA Constructs

The DNA construct was composed of the genetic components described herein and assembled in plasmid vectors (e.g., pYES2, pBAD). Sequences of genes and/or proteins with desired properties were identified in GenBank; these included a gene that encodes sulfotransferase, a gene that encodes UDP-glucuronosyltransferase (UGT), a gene that encodes OGT, a gene that encodes alcohol dehydrogenase, and a gene that encodes cytochrome P450 family 3 subfamily A member 4 (CYP3A4). These sequences were synthesized by CloneTex Systems, Inc. (Austin, TX). Other genetic parts were also obtained for inclusion in the DNA constructs including, for example, promoter genes (e.g., GAL1 promoter), reporter genes (e.g., enhanced green fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzymes' supplier (Promega). The complete insert, containing restriction sites on each end, was then ligated into the plasmid. Successful construction of the insert and ligation of the insert into the plasmid were confirmed by gel electrophoresis.

In some experiments, each gene was PCR amplified using gene-specific overlap primers and assembled sequences were sub-cloned into a pYES2 vector. PCR amplified pieces of all fragments were combined using homologous recombination technology (Gibson Assembly). Clones obtained after transformation were sequenced and analyzed for DNA sequence accuracy.

Figure 1B:
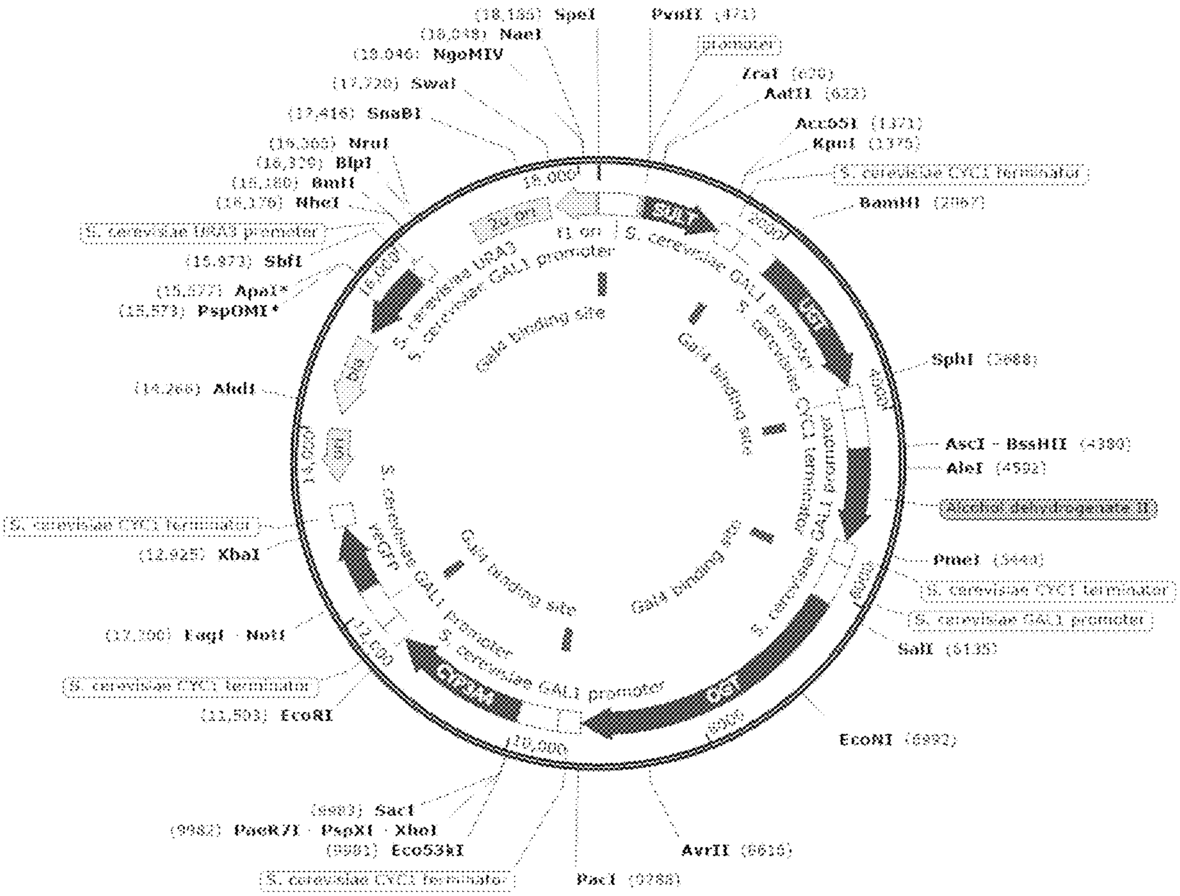

From 5' to 3', one version of the construct for producing an alcohol and opioid detection and/or detoxifying DNA composition or extract includes (a) a gene that encodes sulfotransferase, (b) a gene that encodes UDP-glucuronosyltransferase, (c) a gene that encodes OGT, (d) a gene that encodes alcohol dehydrogenase, (e) a gene that encodes cytochrome P450 family 3 subfamily A member 4 and, (f) a gene that encodes an enhanced green fluorescent protein (FIGS. 1A-1B).

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, Molecular Cloning: A Laboratory Manual, 2nd ed., Vol. 1, Cold Spring Harbor Laboratory Press: Cold Spring Harbor, NY). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm and 280 nm. In order to verify final ligations, DNA was visualized and purified via electrophoresis using a Thermo EC-150 power supply.

The DNA construct was made with gene parts fundamental for expression of sequences such as, for example, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the method described below.

Example 2: Selection of Microorganisms and Development of Competent Cells

Some constructs were produced using transfected yeasts (*Saccharomyces cerevisiae*, ATCC® 200892™). Yeast cells were made competent by subjecting them to an electrochemical process adapted from Gietz and Schiestl (*Nature Protocols,* 2007, 2:35-37). Briefly, a single yeast colony was inoculated into 100 mL YPD (yeast extract peptone dextrose) growth media. Yeast was grown overnight on a shaker at 30° C. to $OD_{600}$=1.0. (Acceptable results were obtained with $OD_{600}$ values ranging from 0.6 to 1.8.) Cells were centrifuged at 2000 rpm in a tabletop centrifuge and resuspended in 10 mL TEL buffer (10 mM Tris-HCl, 1 mM EDTA, 0.1 M LiAc, pH=7.5) and shaken vigorously overnight at room temperature. Alternatively, INVSc1 cells were prepared to be competent using a kit from Sigma-Aldrich, Inc. Cells were again centrifuged and resuspended in 1 mL TEL buffer. Cells prepared in this manner could be stored in the refrigerator for up to one month.

Alternatively, bacterial devices were constructed with one of the following strains of cells: *Escherichia coli*, ONE-SHOT® Top10 competent cells from Life Technologies™, BL21 (DE3) *E. coli* from Novagen, Inc., or DH5α™ *E. coli* from Thermo Fisher Scientific.

Example 3: Transformation of Microbial Cells

Competent cells were stored in the freezer until needed. Cells were thawed on ice and 100 μL of competent cells in TEL buffer were placed in a sterile 1.5 mL microcentrifuge tube. To this was added 5 μL of a 10 mg/mL solution of salmon sperm DNA (carrier DNA). Transforming DNA was added in various amounts. From 1 to 5 μg was sufficient for plasmids from commercial sources, but more DNA was required when transforming yeast with artificial DNA constructs. 10 μL of the DNA device were added to the microcentrifuge tube containing the competent yeast cells and the contents of the tube were mixed. The DNA-yeast suspension was incubated for 30 min at room temperature.

A PLATE solution (consisting of 40% PEG-3350 in 1×TEL buffer) was prepared. 0.7 mL of PLATE solution was added to the DNA-yeast suspension and the contents were mixed thoroughly and incubated for 1 h at room temperature. The mixture was placed in an electromagnetic chamber for 30 minutes. Cells were then heated at 42° C. for 5-10 minutes and 250 μL aliquots were plated on yeast malt agar to which selective growth compounds had been added. Plates were incubated overnight at 30° C.

DNA expression and effectiveness of transformation were determined by fluorescence of the transformed cells expressed in fluorescence units (FSUs) using a 20/20 Luminometer (Promega) according to a protocol provided by the manufacturer. Plasmid DNA extraction, purification, PCR, and gel electrophoresis were also used to confirm transformation. Different transformed devices were obtained. Different types of fluorescent reporter proteins were used (e.g., yellow, red, green, and cyan) for all transformed cells and/or constructs. However, the yellow fluorescent protein was preferred. When no fluorescent reporter protein was assembled, no fluorescence was observed.

*S. cerevisiae* cells were subjected to transformation with the modified pYES2 plasmids for producing metal- and contaminant-binding components as described above. Transformed yeast cells were incubated for 30 min at 28-30° C. Colonies of transformed yeast cells were selected, their DNA isolated and subjected to PCR amplification. Two control treatments were also carried out: (1) a negative control involving competent yeast and nuclease free water instead of a plasmid and (2) a positive control involving competent yeast with unmodified pYES2 plasmid.

Four clones were selected from a transformed plate and processed for full-length DNA sequencing. A clone with 100% DNA sequence accuracy was selected for further processing and was used to obtain a high concentration of plasmid construct at a mid-scale plasmid purification level. Yeast competent cells were transformed with the recombinant plasmid and selected on synthetic complete (SC) dropout plate deficient in uracil. Well isolated clones were isolated and preserved in YPD medium containing 15% glycerol for storage at −80° C.

Example 4: Production of Microbial Extracts and Metabolites

Microbial Extracts Containing Alcohol and Opioid Detecting and/or Detoxifying Metabolites The following non-limiting procedure was used to produce the disclosed extracts:

Method (a) Yeasts transformed with the device depicted in FIGS. 1A-1B were fermented at 37° C. for 48 hours, where culture was conducted with 25 mL of device inoculum in 1 L Luria broth and having 1 μg/mL ampicillin and 100 μM isopropyl-β-D-thiogalactopyranoside (IPTG).
(b) The culture was sterilized by autoclaving at 121° C. for 30 minutes and then centrifuged.
(c) The mixture was filtered with an 0.45 μm filter to produce a supernatant composed of the desired extract.

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be exemplary.

What is claimed is:

1. A DNA construct comprising the following genetic components:
   (a) a gene that encodes a sulfotransferase;
   (b) a gene that encodes a UDP-glucuronosyltransferase (UGT);
   (c) a gene that encodes an O-linked N-acetylglucosamine transferase (OGT);
   (d) a gene that encodes an alcohol dehydrogenase; and
   (e) a gene that encodes a cytochrome P450.

2. The DNA construct of claim 1, wherein the gene that encodes the sulfotransferase has SEQ ID NO. 1 or at least 70% homology thereto.

3. The DNA construct of claim 1, wherein the gene that encodes the UGT has SEQ ID NO. 2 or at least 70% homology thereto.

4. The DNA construct of claim 1, wherein the gene that encodes the OGT has SEQ ID NO. 3 or at least 70% homology thereto.

5. The DNA construct of claim 1, wherein the gene that encodes the alcohol dehydrogenase has SEQ ID NO. 4 or at least 70% homology thereto.

6. The DNA construct of claim 1, wherein the gene that encodes the cytochrome P450 has SEQ ID NO. 5 or at least 70% homology thereto.

7. The DNA construct of claim 1, wherein the construct further comprises at least one promoter.

8. The DNA construct of claim 7, wherein the at least one promoter is a T3 promoter, a T7 promoter, an iron promoter, a GAL1 promoter, or any combination thereof.

9. The DNA construct of claim 8, wherein the at least one promoter is a GAL1 promoter, and the GAL1 promoter is positioned before the gene that encodes the sulfotransferase, UGT, OGT, alcohol dehydrogenase, cytochrome P450, or any combination thereof.

10. The DNA construct of claim 1, wherein the DNA construct further comprises at least one terminator.

11. The DNA construct of claim 10, wherein the at least one terminator is a CYC1 terminator.

12. The DNA construct of claim 1, wherein the DNA construct further comprises a fluorescent reporter protein.

13. The DNA construct of claim 12, wherein the fluorescent reporter protein is a red fluorescent protein, a cyan fluorescent protein, a green fluorescent protein, or a yellow fluorescent protein.

14. The DNA construct of claim 13, wherein the fluorescent reporter protein is a green fluorescent protein.

15. The DNA construct of claim 14, wherein the green fluorescent protein is SEQ ID NO. 6 or has at least 70% homology thereto.

16. The DNA construct of claim 1, wherein the construct comprises from 5' to 3' the following genetic components in the following order: (a) the gene that encodes the sulfotransferase; (b) the gene that encodes the UGT; (c) the gene that encodes the OGT; (d) the gene that encodes the alcohol dehydrogenase; and (e) the gene that encodes the cytochrome P450.

17. The DNA construct of claim 1, wherein the construct comprises from 5' to 3' the following genetic components in the following order: (a) the gene that encodes the sulfotransferase having SEQ ID NO. 1 or at least 70% homology thereto; (b) the gene that encodes the UGT having SEQ ID NO. 2 or at least 70% homology thereto; (c) the gene that encodes the OGT having SEQ ID NO. 3 or at least 70% homology thereto; (d) the gene that encodes the alcohol dehydrogenase having SEQ ID NO. 4 or at least 70% homology thereto; and (e) the gene that encodes the cytochrome P450 having SEQ ID NO. 5 of at least 70% homology thereto.

18. The DNA construct of claim 1, wherein the construct comprises from 5' to 3' the following genetic components in the following order: (a) the gene that encodes the sulfotransferase; (b) a CYC1 terminator; (c) a GAL1 promoter; (d) the gene that encodes the UGT; (e) a CYC1 terminator; (f) a GAL1 promoter; (g) the gene that encodes the OGT; (h) a CYC1 terminator; (i) a GAL1 promoter; (j) the gene that encodes the alcohol dehydrogenase; (k) a CYC1 terminator; (l) a GAL1 promoter; and (m) the gene that encodes the cytochrome P450.

19. The DNA construct of claim 1, wherein the construct comprises from 5' to 3' the following genetic components in the following order: (a) the gene that encodes the sulfotransferase having SEQ ID NO. 1 or at least 70% homology thereto; (b) a CYC1 terminator; (c) a GAL1 promoter; (d) the gene that encodes the UGT having SEQ ID NO. 2 or at least 70% homology thereto; (e) a CYC1 terminator; (f) a GAL1 promoter; (g) the gene that encodes the OGT having SEQ ID NO. 3 or at least 70% homology thereto; (h) a CYC1 terminator; (i) a GAL1 promoter; (j) the gene that encodes the alcohol dehydrogenase having SEQ ID NO. 4 or at least 70% homology thereto; (k) a CYC1 terminator; (l) a GAL1 promoter; and (m) the gene that encodes the cytochrome P450 having SEQ ID NO. 5 or at least 70% homology thereto.

20. The DNA construct of claim 1, wherein the DNA construct has SEQ ID NO. 7.

21. A vector comprising the DNA construct of claim 1.

22. The vector of claim 21, wherein the vector is a plasmid.

23. The vector of claim 22, wherein the plasmid is pWLneo, pSV2cat, pOG44, pXT1, pSG, pSVK3, pBSK, pBSKII, pYES, pYES2, pET, pUC, or pUC19.

24. The vector of claim 23, wherein the vector is pYES2.

25. A biological device comprising host cells transformed with the DNA construct of claim 1.

26. The device of claim 25, wherein the host cells comprise fungi or bacteria.

27. The device of claim 26, wherein the fungi comprise *Saccharomyces cerevisiae*.

28. A method for producing a composition for detecting or detoxifying alcohol or opioids, the method comprising growing the biological device of claim 25 for a time sufficient to produce the composition.

29. The method of claim 28, wherein after growing the biological device to produce the composition, the method further comprises the step of lysing the host cells in the composition to produce a lysed composition.

30. A composition produced by the method of claim 28.

* * * * *

SEQUENCE LISTING

```
Sequence total quantity: 7
SEQ ID NO: 1            moltype = DNA  length = 858
FEATURE                 Location/Qualifiers
source                  1..858
                        mol_type = other DNA
                        organism = synthetic construct
SEQUENCE: 1
atgtcagacg actttctttg gttcgagggt atcgctttcc caacaatggg attcagatcc  60
gaaacactta gaaaggttag ggatgagttt gtgatccgtg atgaagacgt cattatcctt  120
acttacccaa agtcaggtac aaattggctt gctgaaatct tgtgtttgat gcactctaaa  180
ggagacgcaa agtggattca atctgtccct atttgggaga gatcaccttg ggtcgagtct  240
gagatcggtt acacagcctt atctgaaaca gaatctccaa ggctgttctc cagtcacctt  300
cctatccaat tgtttcctaa gagtttcttt agttcaaagg ctaaggtcat ctacttaatg  360
agaaacccaa gagacgtatt ggtttcagga tacttcttct ggaagaacat gaaattcatc  420
aagaaaccca agtcttggga ggagtacttc gagtggttct gtcaaggaac tgtgctgtat  480
ggttcctggt ttgatcatat acacggttgg atgccaatga gagaagagaa gaacttctta  540
ctgttgtcat acgaggagtt gaaacaggat actggtagga ctattgagaa gatatgccag  600
tttctgggaa agaccctgga accagaagaa ttgaacttaa tcttgaagaa tagtagtttc  660
caatccatga aagagaataa gatgtccaac tactcattgc tttctgttga ttacgtcgtt  720
gacaaagcac agttacttag aaagggtgtt agtggagatt ggaagaatca ctttaccgtt  780
gctcaggctg aggactttga taaactgttc caagagaaga tggctgattt gccaagagaa  840
ttgtttccat gggaatag                                                858

SEQ ID NO: 2            moltype = DNA  length = 1562
FEATURE                 Location/Qualifiers
source                  1..1562
                        mol_type = other DNA
                        organism = synthetic construct
SEQUENCE: 2
atggctcgtg gattgcaagt tcctttacct agattagcta ctggactgtt gcttctgttg  60
tccgttcaac catgggctga atcaggaaag gtcttagtgg tgcccaccga tggttctcct  120
tggttgtcta tgagagaggc attaagagaa ttgcacgcca gaggacatca agctgttgtc  180
ttgacaccag aagtaaacat gcatatcaag gaggagaagt tctttacatt gacagcctat  240
gctgtcccat ggacacagaa ggagttcgat agagttacat tgggttatac acaaggattc  300
ttcgagactg aacacttatt gaagagatat tcccgttcta tggccataat gaataacgtg  360
tccctggcct tgcatagatg ttgcgttgaa ttgctgcata atgaggcttt gatccgtcac  420
ttgaacgcca cttcctttga tgtagtcttg accgacccag ttaacctgtg cggagccgtt  480
ctggccaagt atctgagtat cccagccgtc ttcttctgga gatacatccc ttgtgactta  540
gatttcaagg gaactcaatg tcccaatcca tcttcttaca tccctaagtt gttaaccacc  600
aactctgatc acatgacctt tcttcaaagg gtgaagaata tgttataccc actggctctg  660
tcatacatct gtcatacttt ctctgcacca tacgccagtc ttgcttctga gttgttccaa  720
agagaggttt ccgtagttga cttggtttca tacgcctccg tctggttgtt cagaggtgat  780
ttcgttatgg attatcctag acccataatg cctaacatgg tgtttatcgg tggaatcaat  840
tgtgctaatg gtaaaccttt aagtcaagag ttcgaagcat acatcaacgc aagtggtgaa  900
catggtatag tcgtcttctc tttgggttcc atggtgtcag agatccctga gaagaaggct  960
atggccatcg ctgacgctct tggaaagata ccacagactg ttctttggag atatactggt  1020
actcgtccat ccaatttggc taacaacact attcttgtaa agtggttgcc tcagaacgat  1080
ttgttgggac acccaatgac aagagctttc attacccatg ctggatctca cggtgtttat  1140
gaatctatct gcaacggtgt tccaatggtt atgatgccac tgtttggtga tcagatggat  1200
aatgctaaga gaatggaaac taagggtgct ggtgttacct tgaatgtctt ggaaatgacc  1260
tccgaagact tggagaatgc tttgaaagct gttatcaatg acaagtcata caaggagaac  1320
attatgagat tatccagtct gcataaagat agaccagttg agccactgga tctggcagtg  1380
ttctgggttg agttcgtgat gaggcacaaa ggagcaccac atcttagacc tgctgcccat  1440
gacctgactt ggtatcagta ccattctctt gacgtgatcg gtttcttgtt agcagtcgtg  1500
cttacagtgg ctttcatcac ctttaagtgc tgcgcttacg gttacaggaa gtgtctgggt  1560
aa                                                                 1562

SEQ ID NO: 3            moltype = DNA  length = 1047
FEATURE                 Location/Qualifiers
source                  1..1047
                        mol_type = other DNA
                        organism = synthetic construct
SEQUENCE: 3
atgtctattc cagaaactca aaaagccatt atcttctacg aatccaacgg caagttggag  60
cataaggata tcccagttcc aaagccaaag cccaacgaat tgttaatcaa cgtcaagtac  120
tctggtgtct gccacaccga tttgcacgct tggcatggtg actggccatt gccaactaag  180
ttaccattag ttggtggtca cgaaggtgcc ggtgtcgttg tcggcatggg tgaaaacgtt  240
aagggctgga agatcggtga ctacgccggt atcaaatggt tgaacggttc ttgtatggcc  300
tgtgaatact gtgaattggg taacgaatcc aactgtcctc acgctgactt gtctggttac  360
acccacgacg gttctttcca agaatacgct accgctgacg ctgttcaagc cgctcacatt  420
cctcaaggta ctgacttggc tgaagtcgcg ccaatcttgt gtgctggtat caccgtatac  480
```

```
aaggctttga agtctgccaa cttgagagca ggccactggg cggccatttc tggtgctgct  540
ggtggtctag gttctttggc tgttcaatat gctaaggcga tgggttacag agtcttaggt  600
attgatggtg gtccaggaaa ggaagaattg tttacctcgc tcggtggtga agtattcatc  660
gacttcacca aagagaagga cattgttagc gcagtcgtta aggctaccaa cggcggtgcc  720
cacggtatca tcaatgtttc cgtttccgaa gccgctatcg aagcttctac cagatactgt  780
agggcgaacg gtactgttgt cttggttggt ttgccagccg gtgcaaagtg ctcctctgat  840
gtcttcaacc acgttgtcaa gtctatctcc attgtcggct cttacgtggg gaacagagct  900
gataccagag aagccttaga tttctttgcc agaggtctag tcaagtctcc aataaaggta  960
gttggcttat ccagtttacc agaaatttac gaaaagatgg agaagggcca aattgctggt  1020
agatacgttg ttgacacttc taaataa                                      1047

SEQ ID NO: 4            moltype = DNA  length = 3141
FEATURE                 Location/Qualifiers
source                  1..3141
                        mol_type = other DNA
                        organism = synthetic construct
SEQUENCE: 4
atggcttcat ctgttggaaa tgttgccgat tctactgaac ctaccaagag aatgttatca  60
tttcaaggat tagctgaatt agcccatagg gaataccaag ccggtgactt tgaagctgcc  120
gaaagacact gtatgcaatt gtggagacag gagccagaca atacaggcgt gttattgttg  180
ttgtcatcta ttcatttcca atgtagaagg ttggatagat ctgctcactt tagtactttg  240
gcaatcaaac agaatccatt gttagctgaa gcatattcca acttaggtaa cgtctataag  300
gaaagaggtc aattgcagga agccatcgag cattaccgtc atgcattaag attgaagccc  360
gatttcatcg atggttacat taacttagca gcagccttgg ttgcagcagg agatatggaa  420
ggtgcagtcc aagcctatgt ctccgcatta cagtataacc ctgacttgta ctgtgttaga  480
tctgatttgg gaaacttatt gaaggcattg ggaaggttgg aagaggcaaa ggcttgctac  540
ttgaaggcca tagaaactca accaaacttc gcagtcgcat ggtcaaactt gggttgcgtg  600
ttcaacgcac aaggtgaaat ctggttagct atccaccatt tcgagaaagc agttacttta  660
gatcccaatt tcttggatgc ctacatcaat ttgggaaatg tgttaaagga ggcaaggatc  720
ttcgaccgtg ctgtcgcagc atacttaagg gctttgtctt taagtccaaa ccacgcagtt  780
gtacatggca acttggcttg tgtctactat gagcaaggat tgattgactt agctattgat  840
acctatcgta gggccattga attacagcca cactttcctg acgcttactg caacttggct  900
aatgccttga aggagaaggg atctgtggca gaggctgagg attgctacaa caccgcattg  960
aggttatgtc caacacatgc agattcctta aacaatttgg ccaatatcaa gcgtgaacag  1020
ggtaacatcg aagaagccgt cagattgtat agaaaggcct tagaggtctt tcctgaattt  1080
gctgctgccc attccaactt agcaagtgtg ttacagcagc aaggcaagtt gcaagaagcc  1140
ttaatgcact ataaggaagc aatcagaata agtcctacct ttgccgatgc ttattccaat  1200
atgggtaata ctttgaagga aatgcaggat gtccaaggtg ccttacaatg ttataccagg  1260
gcaattcaaa tcaatcctgc tttcgcagat gctcattcta acttggcatc catccataaa  1320
gattcaggca acataccaga ggccatcgcc tcttatcgta cagccttgaa gttgaagcct  1380
gatttcccag atgcctattg caacttggcc cattgtttgc aaattgtatg tgattggaca  1440
gattacgatg aaagaatgaa gaagttggtg agtatcgttg ctgaccaatt agagaagaac  1500
agattgccat cagttcaccc tcatcactct atgttgtacc cattgagtca tggtttcaga  1560
aaggcaattg ctgaaaggca tggcaatttg tgtttggaca agatcaatgt cttacataag  1620
cctccatacg aacatcctaa ggatttgaaa ttgtcagatg gaaggttgcg tgtcggatat  1680
gtttcttctg atttcggtaa tcatccaacc agtcacttaa tgcagagtat ccctggtatg  1740
cataatcccg acaaattcga agtcttctgt tatgccttaa gtccagatga cggcaccaat  1800
ttcagagtga aagttatggc tgaagctaat catttcattg atttgagtca aattccttgt  1860
aacggtaaag ccgcagatag gatacaccaa gacggcattc atatcttggt caatatgaac  1920
ggatacacaa agggtgctag aaacgagttg tttgctttaa gaccagcacc tatacaagca  1980
atgtggttag gctatccagg cacttcaggt gctttgttca tggactacat cataaccgac  2040
caagaaactt ctcccgcaga ggttgctgaa caatacagtg agaagttggc ttacatgcca  2100
catactttct tcattggtga tcatgccaat atgttcccac atttgaagaa gaaagcagtc  2160
atagatttca aatctaatgg acatatctat gataacagaa tagtgttaaa cggtattgat  2220
ttgaaagcat tcttggattc cttacctgat gttaagattg ttaagatgaa gtgtccagat  2280
ggtggcgaca acgctgattc ttctaatacc gctttgaata tgcctgtgat cccaatgaat  2340
actatcgccg aggcagttat cgaaatgatc aatagaggcc aaattcaaat cacaatcaat  2400
ggattctcta tttctaacgg tttagcaaca acacagataa acaacaaagc tgctaccgga  2460
gaagaggtgc ctaggaccat tatcgttact acaagatccc agtatggttt acctgaggac  2520
gctatcgtgt actgcaactt caatcagtta tacaagatcg atccttcaac cttacagatg  2580
tgggctaaca tcttgaagag ggttcccaat tcagtattgt ggttgttaag atttcccgca  2640
gtcggtgagc ctaacattca acagtacgct cagaatatgg gcttacctca gaatagaatc  2700
atattctctc ctgtagctcc aaaggaagaa catgtcagac gtggtcaatt ggccgatgtg  2760
tgtttggaca ctcccttgtg caacggacac accactggta tggatgtctt gtgggcaggc  2820
actcctatgg taactatgcc tggcgaaaca ttggctagta gagttgcagc tagtcaattg  2880
acatgcttag gttgcttaga gttgattgca aagaacagac aagaatacga agatattgct  2940
gtcaagttag gtactgattt ggagtacttg aagaaggtta gaggtaaggt ctggaaacaa  3000
agaattagta gtccattgtt caacaccaaa caatacacaa tggaattaga aagattgtac  3060
ttacaaatgt gggagcacta tgccgcaggt aacaaacctg accacatgat caaaccagtt  3120
gaagtaaccg aatccgctta a                                            3141

SEQ ID NO: 5            moltype = DNA  length = 1509
FEATURE                 Location/Qualifiers
source                  1..1509
                        mol_type = other DNA
                        organism = synthetic construct
SEQUENCE: 5
atggctttga ttcccgacct tgctatggaa acctggctgt tgttggctgt ttctcttgtc  60
ttgttgtact tgtatggaac ccatagtcat ggtctgttca agaagttggg aatacctgga  120
```

```
cctactccat taccatttct gggtaacatc ctgagttacc ataaaggttt ctgtatgttc  180
gacatggaat gtcataagaa gtatggtaaa gtttggggtt tctacgatgg tcaacaacca  240
gtattggcca ttactgatcc cgatatgata aagactgtat tggtaaagga gtgctattcc  300
gtattcacta acagaagacc attcggacca gtgggattca tgaagtctgc aatttccatt  360
gcagaagacg aagagtggaa gaggttaaga tcattgcttt caccaacctt tacatcagga  420
aagttgaagg aaatggtgcc catcatcgct cagtatggtg atgttcttgt gagaaacctt  480
agaagagaag ctgaaaccgg aaagcctgtt acattgaaag acgtgttcgg tgcttattca  540
atggatgtta tcacatcaac atctttcggt gtcaacattg attcattgaa taaccctcag  600
gacccattcg tagagaacac taagaaattg cttagattcg atttcctgga ccctttcttc  660
ttatccatta tcttcccttt ccttattcct atcttggagg tgttgaacat ctgcgtgttc  720
ccaagagaag taacaaactt ccttagaaag tcagtgaaga ggatgaaaga gagtcgtctg  780
gaggataccc agaagcatag agtggacttc ttgcagttga tgatagattc ccagaactct  840
aaagaaacag aatcacataa ggctttgtcc gacttggagt tggtagccca atccatcatc  900
ttcatcttcg caggttatga gacaacttca tccgtactgt cattcattat gtatgaattg  960
gctactcacc ctgatgttca acagaagtta caagaagaga ttgatgctgt actgcccaat  1020
aaggcaccac ctacctacga cactgtcctt caaatggaat acttagacat ggttgtcaac  1080
gagacattga gattgtttcc aattgcaatg cgtctggaaa gagtctgcaa gaaggatgtt  1140
gaaatcaacg gtatgtttat ccctaagggt gttgtagtta tgatcccatc atacgctctg  1200
catagagatc caaagtactg gactgaacct gagaagttcc tgccagagag attctctaag  1260
aagaataagg acaacataga tccctacata tacactccct tcggatctgg tccaagaaac  1320
tgtattggta tgagattcgc tcttatgaat atgaagttag ccctgattag agtcttacag  1380
aacttctcct ttaagccatg taaggaaacc cagataccac tgaaactttc tcttggtgga  1440
ttgttgcagc cagagaaacc cgttgttctg aaggtagagt caagagatgg tacagtgtca  1500
ggtgcctga                                                         1509

SEQ ID NO: 6            moltype = DNA  length = 717
FEATURE                 Location/Qualifiers
source                  1..717
                        mol_type = other DNA
                        organism = synthetic construct
SEQUENCE: 6
atgtctaaag gtgaagaatt attcactggt gttgtcccaa ttttggttga attagatggt  60
gatgttaatg gtcacaaatt ttctgtctcc ggtgaaggtg aaggtgatgc tacttacggt  120
aaattgacct taaaatttat ttgtactact ggtaaattgc cagttccatg gccaacctta  180
gtcactactt tcggttatgg tgttcaatgt tttgctagat acccagatca tatgaaacaa  240
catgactttt tcaagtctgc catgccagaa ggttatgttc aagaaagaac tatttttttc  300
aaagatgacg gtaactacaa gaccagagct gaagtcaagt ttgaaggtga taccttagtt  360
aatagaatcg aattaaaagg tattgatttt aaagaagatg gtaacatttt aggtcacaaa  420
ttggaataca actataactc tcacaatgtt tacatcatgg ctgacaaaca aaagaatggt  480
atcaaagtta acttcaaaat tagacacaac attgaagatg gttctgttca attagctgac  540
cattatcaac aaaatactcc aattggtgat ggtccagtct tgttaccaga caaccattac  600
ttatccactc aatctgcctt atccaaagat ccaaacgaaa agagagacca catggtcttg  660
ttagaatttg ttactgctgc tggtattacc catggtatgg atgaattgta caaataa     717

SEQ ID NO: 7            moltype = DNA  length = 18193
FEATURE                 Location/Qualifiers
source                  1..18193
                        mol_type = other DNA
                        organism = synthetic construct
SEQUENCE: 7
acggattaga agccgccgag cgggtgacag ccctccgaag gaagactctc ctccgtgcgt  60
cctcgtcttc accggtcgcg ttcctgaaac gcagatgtgc ctcgcgccgc actgctccga  120
acaataaaga ttctacaata ctagctttta tggttatgaa gaggaaaaat tggcagtaac  180
ctggccccac aaaccttcaa atgaacgaat caaattaaca accataggat gataatgcga  240
ttagtttttt agccttattt ctggggtaat taatcagcga agcgatgatt tttgatctat  300
taacagatat ataaatgcaa aaactgcata accactttaa ctaatacttt caacattttc  360
ggtttgtatt acttcttatt caaatgtaat aaaagtatca acaaaaaatt gttaatatac  420
ctctatactt taacgtcaag gagaaaaaac cccggatcgg actactagca gctgtaatac  480
gactcactat agggaatatt aagcttgcca ccatgtcaga cgactttctt tggttcgagg  540
gtatcgcttt cccaacaatg ggattcagat ccgaaacact tagaaaggtt agggatgagt  600
ttgtgatccg tgatgaagac gtcattatcc ttacttaccc aaagtcaggt acaaattggc  660
ttgctgaaat cttgtgtttg atgcactcta aggagacgc aaagtggatt caatctgtcc  720
ctatttggga gagatcacct tgggtcgagt ctgagatcgg ttacacagcc ttatctgaaa  780
cagaatctcc aaggctgttc tccagtcacc ttcctatcca attgtttcct aagagtttct  840
ttagttcaaa ggctaaggtc atctacttaa tgagaaaccc aagagacgta ttggtttcag  900
gatacttctt ctggaagaac atgaaattca tcaagaaacc caagtcttgg gaggagtact  960
tcgagtggtt ctgtcaagga actgtgctgt atggttcctg gtttgatcat atacacggtt  1020
ggatgccaat gagagaagag aagaacttct tactgttgtc atacgaggag ttgaaacagg  1080
atactggtag gactattgag aagatatgcc agtttctggg aaagaccctg gaaccagaag  1140
aattgaactt aatcttgaag aatagtagtt tccaatccat gaaagagaat aagatgtcca  1200
actactcatt gctttctgtt gattacgtcg ttgacaaagc acagttactt agaaagggtg  1260
ttagtggaga ttggaagaat cactttaccg ttgctcaggc tgaggacttt gataaactgt  1320
tccaagagaa gatggctgat ttgccaagag aattgtttcc atgggaatag ggtacctcat  1380
gtaattagtt atgtcacgct tacattcacg ccctcccccc acatccgctc taaccgaaaa  1440
ggaaggagtt agacaacctg aagtctaggt ccctatttat ttttttatag ttatgttagt  1500
attaagaacg ttatttatat ttcaaatttt tctttttttt ctgtacagac gcgtgtacgc  1560
atgtaacatt atactgaaaa ccttgcttga gaaggttttg ggacgctcga aggctttaat  1620
ttgccggatt agaagccgcc gagcgggtga cagccctccg aaggaagact ctcctccgtg  1680
cgtcctcgtc ttcaccggtc gcgttcctga aacgcagatg tgcctcgcgc cgcactgctc  1740
```

```
cgaacaataa agattctaca atactagctt ttatggttat gaagaggaaa aattggcagt  1800
aacctggccc cacaaacctt caaatgaacg aatcaaatta acaaccatag gatgataatg  1860
cgattagttt tttagcctta tttctggggt aattaatcag cgaagcgatg atttttgatc  1920
tattaacaga tatataaatg caaaaactgc ataaccactt taactaatac tttcaacatt  1980
ttcggtttgt attacttctt attcaaatgt aataaaagta tcaacaaaaa attgttaata  2040
tacctctata ctttaacgtc aaggagggat ccgccaccat ggctcgtgga ttgcaagttc  2100
ctttacctag attagctact ggactgttgc ttctgttgtc cgttcaacca tgggctgaat  2160
caggaaaggt cttagtggtg cccaccgatg gttctccttg gttgtctatg agagaggcat  2220
taagagaatt gcacgccaga ggacatcaag ctgttgtctt gacaccagaa gtaaacatgc  2280
atatcaagga ggagaagttc tttacattga cagcctatgc tgtcccatgg acacagaagg  2340
agttcgatag agttacattg ggttatacac aaggattctt cgagactgaa cacttattga  2400
agagatattc ccgttctatg gccataatga ataacgtgtc cctggccttg catagatgtt  2460
gcgttgaatt gctgcataat gaggctttga tccgtcactt gaacgccact tcctttgatg  2520
tagtcttgac cgacccagtt aacctgtgcg gagccgttct ggccaagtat ctgagtatcc  2580
cagccgtctt cttctggaga tacatccctt gtgacttaga tttcaaggga actcaatgtc  2640
ccaatccatc ttcttacatc cctaagttgt taaccaccaa ctctgatcac atgacctttc  2700
ttcaaagggt gaagaatatg ttatacccac tggctctgtc atacatctgt catactttct  2760
ctgcaccata cgccagtctt gcttctgagt tgttccaaag agaggtttcc gtagttgact  2820
tggtttcata cgcctccgtc tggttgttca gaggtgattt cgttatggat tatcctagac  2880
ccataatgcc taacatggtg tttatcggtg gaatcaattg tgctaatggt aaacctttaa  2940
gtcaagagtt cgaagcatac atcaacgcaa gtggtgaaca tggtatagtc gtcttctctt  3000
tgggttccat ggtgtcagag atccctgaga agaaggctat ggccatcgct gacgctcttg  3060
gaaagatacc acagactgtt ctttggagat atactggtac tcgtccatcc aatttggcta  3120
acaacactat tcttgtaaag tggttgcctc agaacgattt gttgggacac ccaatgacaa  3180
gagctttcat tacccatgct ggatctcacg gtgtttatga atctatctgc aacggtgttc  3240
caatggttat gatgccactg tttggtgatc agatggataa tgctaagaga atggaaacta  3300
agggtgctgg tgttaccttg aatgtcttgg aaatgacctc cgaagacttg gagaatgctt  3360
tgaaagctgt tatcaatgac aagtcataca aggagaacat tatgagatta tccagtctgc  3420
ataaagatag accagttgag ccactggatc tggcagtgtt ctgggttgag ttcgtgatga  3480
ggcacaaagg agcaccacat cttagacctg ctgcccatga cctgacttgg tatcagtacc  3540
attctcttga cgtgatcggt ttcttgttag cagtcgtgct tacagtggct ttcatcacct  3600
ttaagtgctg cgcttacggt tacaggaagt gtctgggtaa gaaaggaaga gtgaagaagg  3660
cacataagtc caagactcat tgagcatgct catgtaatta gttatgtcac gcttacattc  3720
acgccctccc cccacatccg ctctaaccga aaaggaagga gttagacaac ctgaagtcta  3780
ggtccctatt tattttttta tagttatgtt agtattaaga acgttattta tatttcaaat  3840
tttttctttt tttctgtaca gacgcgtgta cgcatgtaac attatactga aaaccttgct  3900
tgagaaggtt ttgggacgct cgaaggcttt aatttgccgg attagaagcc gccgagcggg  3960
tgacagccct ccgaaggaag actctcctcc gtgcgtcctc gtcttcaccg gtcgcgttcc  4020
tgaaacgcag atgtgcctcg cgccgcactg ctccgaacaa taaagattct acaatactag  4080
cttttatggt tatgaagagg aaaaattggc agtaacctgg ccccacaaac cttcaaatga  4140
acgaatcaaa ttaacaacca taggatgata atgcgattag tttttagcc ttatttctgg  4200
ggtaattaat cagcgaagcg atgatttttg atctattaac agatatataa atgcaaaaac  4260
tgcataacca ctttaactaa tactttcaac attttcggtt tgtattactt cttattcaaa  4320
tgtaataaaa gtatcaacaa aaaattgtta atatacctct atactttaac gtcaaggagg  4380
cgcgccacca tgtctattcc agaaactcaa aaagccatta tcttctacga atccaacggc  4440
aagttggagc ataaggatat cccagttcca aagccaaagc ccaacgaatt gttaatcaac  4500
gtcaagtact ctggtgtctg ccacaccgat ttgcacgctt ggcatggtga ctggccattg  4560
ccaactaagt taccattagt tggtggtcac gaaggtgccg gtgtcgttgt cggcatgggt  4620
gaaaacgtta agggctggaa gatcggtgac tacgccggta tcaaatggtt gaacggttct  4680
tgtatggcct gtgaatactg tgaattgggt aacgaatcca actgtcctca cgctgacttg  4740
tctggttaca cccacgacgg ttctttccaa gaatacgcta ccgctgacgc tgttcaagcc  4800
gctcacattc ctcaaggtac tgacttggct gaagtcgcgc caatcttgtg tgctggtatc  4860
accgtataca aggctttgaa gtctgccaac ttgagagcag gccactgggc ggccatttct  4920
ggtgctgctg gtggtctagg ttctttggct gttcaatatg ctaaggcgat gggttacaga  4980
gtcttaggta ttgatggtgg tccaggaaag gaagaattgt ttacctcgct cggtggtgaa  5040
gtattcatcg acttcaccaa agagaaggac attgttagcg cagtcgttaa ggctaccaac  5100
ggcggtgccc acggtatcat caatgtttcc gtttccgaag ccgctatcga agcttctacc  5160
agatactgta gggcgaacgg tactgttgtc ttggttggtt tgccagccgg tgcaaagtgc  5220
tcctctgatg tcttcaacca cgttgtcaag tctatctcca ttgtcggctc ttacgtgggg  5280
aacagagctg ataccagaga agccttagat ttctttgcca gaggtctagt caagtctcca  5340
ataaaggtag ttggcttatc cagtttacca gaaatttacg aaaagatgga gaagggccaa  5400
attgctggta gatacgttgt tgacacttct aaataagttt aaactcatgt aattagttat  5460
gtcacgctta cattcacgcc ctccccccac atccgctcta accgaaaagg aaggagttag  5520
acaacctgaa gtctaggtcc ctatttattt ttttatagtt atgttagtat taagaacgtt  5580
atttatattt caaatttttc ttttttttct gtacagacgc gtgtacgcat gtaacattat  5640
actgaaaacc ttgcttgaga aggttttggg acgctcgaag gctttaattt gccggattag  5700
aagccgccga gcgggtgaca gccctccgaa ggaagactct cctccgtgcg tcctcgtctt  5760
caccggtcgc gttcctgaaa cgcagatgtg cctcgcgccg cactgctccg aacaataaag  5820
attctacaat actagctttt atggttatga agaggaaaaa ttggcagtaa cctggcccca  5880
caaaccttca aatgaacgaa tcaaattaac aaccatagga tgataatgcg attagttttt  5940
tagccttatt tctggggtaa ttaatcagcg aagcgatgat tttgatcta ttaacagata  6000
tataaatgca aaaactgcat aaccacttta actaatactt tcaacatttt cggtttgtat  6060
tacttcttat tcaaatgtaa taaaagtatc aacaaaaaat tgttaatata cctctatact  6120
ttaacgtcaa ggaggtcgac gccaccatgg cttcatctgt tggaaatgtt gccgattcta  6180
ctgaacctac caagagaatg ttatcatttc aaggattagc tgaattagcc catagggaat  6240
accaagccgg tgactttgaa gctgccgaaa gacactgtat gcaattgtgg agacaggagc  6300
cagacaatac aggcgtgtta ttgttgttgt catctattca tttccaatgt agaaggttgg  6360
atagatctgc tcactttagt actttggcaa tcaaacagaa tccattgtta gctgaagcat  6420
attccaactt aggtaacgtc tataaggaaa gaggtcaatt gcaggaagcc atcgagcatt  6480
```

-continued

```
accgtcatgc attaagattg aagcccgatt tcatcgatgg ttacattaac ttagcagcag  6540
ccttggttgc agcaggagat atggaaggtg cagtccaagc ctatgtctcc gcattacagt  6600
ataaccctga cttgtactgt gttagatctg atttgggaaa cttattgaag gcattgggaa  6660
ggttggaaga ggcaaaggct tgctacttga aggccataga aactcaacca aacttcgcag  6720
tcgcatggtc aaacttgggt tgcgtgttca acgcacaagg tgaaatctgg ttagctatcc  6780
accatttcga gaaagcagtt actttagatc ccaatttctt ggatgcctac atcaatttgg  6840
gaaatgtgtt aaaggaggca aggatcttcg accgtgctgt cgcagcatac ttaagggctt  6900
tgtctttaag tccaaaccac gcagttgtac atggcaactt ggcttgtgtc tactatgagc  6960
aaggattgat tgacttagct attgatacct atcgtagggc cattgaatta cagccacact  7020
ttcctgacgc ttactgcaac ttggctaatg ccttgaagga gaagggatct gtggcagagg  7080
ctgaggattg ctacaacacc gcattgaggt tatgtccaac acatgcagat tccttaaaca  7140
atttggccaa tatcaagcgt gaacagggta acatcgaaga agccgtcaga ttgtatagaa  7200
aggccttaga ggtctttcct gaatttgctg ctgcccattc caacttagca agtgtgttac  7260
agcagcaagg caagttgcaa gaagccttaa tgcactataa ggaagcaatc agaataagtc  7320
ctacctttgc cgatgcttat tccaatatgg gtaatacttt gaaggaaatg caggatgtcc  7380
aaggtgcctt acaatgttat accagggcaa ttcaaatcaa tcctgctttc gcagatgctc  7440
attctaactt ggcatccatc cataaagatt caggcaacat accagaggcc atcgcctctt  7500
atcgtacagc cttgaagttg aagcctgatt tcccagatgc ctattgcaac ttggcccatt  7560
gtttgcaaat tgtatgtgat tggacagatt acgatgaaag aatgaagaag ttggtgagta  7620
tcgttgctga ccaattagag aagaacagat tgccatcagt tcaccctcat cactctatgt  7680
tgtacccatt gagtcatggt ttcagaaagg caattgctga aaggcatggc aatttgtgtt  7740
tggacaagat caatgtctta cataagcctc catacgaaca tcctaaggat ttgaaattgt  7800
cagatggaag gttgcgtgtc ggatatgttt cttctgattt cggtaatcat ccaaccagtc  7860
acttaatgca gagtatccct ggtatgcata atcccgacaa attcgaagtc ttctgttatg  7920
ccttaagtcc agatgacggc accaatttca gagtgaaagt tatggctgaa gctaatcatt  7980
tcattgattt gagtcaaatt ccttgtaacg gtaaagccgc agataggata caccaagacg  8040
gcattcatat cttggtcaat atgaacggat acacaaaggg tgctagaaac gagttgtttg  8100
ctttaagacc agcacctata caagcaatgt ggttaggcta tccaggcact tcaggtgctt  8160
tgttcatgga ctacatcata accgaccaag aaacttctcc cgcagaggtt gctgaacaat  8220
acagtgagaa gttggcttac atgccacata ctttcttcat tggtgatcat gccaatatgt  8280
tcccacattt gaagaagaaa gcagtcatag atttcaaatc taatggacat atctatgata  8340
acagaatagt gttaaacggt attgatttga aagcattctt ggattcctta cctgatgtta  8400
agattgttaa gatgaagtgt ccagatggtg gcgacaacgc tgattcttct aataccgctt  8460
tgaatatgcc tgtgatccca atgaatacta tcgccgaggc agttatcgaa atgatcaata  8520
gaggccaaat tcaaatcaca atcaatggat tctctatttc taacggttta gcaacaacac  8580
agataaacaa caaagctgct accggagaag aggtgcctag gaccattatc gttactacaa  8640
gatcccagta tggtttacct gaggacgcta tcgtgtactg caacttcaat cagttataca  8700
agatcgatcc ttcaacctta cagatgtggg ctaacatctt gaagagggtt cccaattcag  8760
tattgtggtt gttaagattt cccgcagtcg gtgagcctaa cattcaacag tacgctcaga  8820
atatgggctt acctcagaat agaatcatat tctctcctgt agctccaaag gaagaacatg  8880
tcagacgtgg tcaattggcc gatgtgtgtt tggacactcc cttgtgcaac ggacacacca  8940
ctggtatgga tgtcttgtgg gcaggcactc ctatggtaac tatgcctggc gaaacattgg  9000
ctagtagagt tgcagctagt caattgacat gcttaggttg cttagagttg attgcaaaga  9060
acagacaaga atacgaagat attgctgtca agttaggtac tgatttggag tacttgaaga  9120
aggttagagg taaggtctgg aaacaaagaa ttagtagtcc attgttcaac accaaacaat  9180
acacaatgga attagaaaga ttgtacttac aaatgtggga gcactatgcc gcaggtaaca  9240
aacctgacca catgatcaaa ccagttgaag taaccgaatc cgcttaatta atcatgtaat  9300
tagttatgtc acgcttacat tcacgccctc cccccacatc cgctctaacc gaaaaggaag  9360
gagttagaca acctgaagtc taggtcccta tttatttttt tatagttatg ttagtattaa  9420
gaacgttatt tatatttcaa atttttcttt tttttctgta cagacgcgtg tacgcatgta  9480
acattatact gaaaaccttg cttgagaagg ttttgggacg ctcgaaggct ttaatttgcc  9540
ggattagaag ccgccgagcg ggtgacagcc ctccgaagga agactctcct ccgtgcgtcc  9600
tcgtcttcac cggtcgcgtt cctgaaacgc agatgtgcct cgcgccgcac tgctccgaac  9660
aataaagatt ctacaatact agcttttatg gttatgaaga ggaaaaattg gcagtaacct  9720
ggccccacaa accttcaaat gaacgaatca aattaacaac cataggatga taatgcgatt  9780
agttttttag ccttatttct ggggtaatta atcagcgaag cgatgatttt tgatctatta  9840
acagatatat aaatgcaaaa actgcataac cactttaact aatactttca acattttcgg  9900
tttgtattac ttcttattca aatgtaataa aagtatcaac aaaaaattgt taatatacct  9960
ctatacttta acgtcaagga gctcgaggcc accatggctt tgattcccga ccttgctatg  10020
gaaacctggc tgttgttggc tgtttctctt gtcttgttgt acttgtatgg aacccatagt  10080
catggtctgt tcaagaagtt gggaataccc ggacctactc cattaccatt tctgggtaac  10140
atcctgagtt accataaagg tttctgtatg ttcgacatgg aatgtcataa gaagtatggt  10200
aaagtttggg gtttctacga tggtcaacaa ccagtattgg ccattactga tcccgatatg  10260
ataaagactg tattggtaaa ggagtgctat tccgtattca ctaacagaag accattcgga  10320
ccagtgggat tcatgaagtc tgcaatttcc attgcagaag acgaagagtg gaagaggtta  10380
agatcattgc tttcaccaac ctttacatca ggaaagttga aggaaatggt gcccatcatc  10440
gctcagtatg gtgatgttct tgtgagaaac cttagaagag aagctgaaac cggaaagcct  10500
gttacattga aagacgtgtt cggtgcttat tcaatggatg ttatcacatc aacatctttc  10560
ggtgtcaaca ttgattcatt gaataaccct caggacccat tcgtagagaa cactaagaaa  10620
ttgcttagat tcgatttcct ggaccctttc ttcttatcca ttatcttccc tttccttatt  10680
cctatcttgg aggtgttgaa catctgcgtg ttcccaagag aagtaacaaa cttccttaga  10740
aagtcagtga agaggatgaa agagagtcgt ctggaggata cccagaagca tagagtggac  10800
ttcttgcagt tgatgataga ttcccagaac tctaaagaaa cagaatcaca taaggctttg  10860
tccgacttgg agttggtagc ccaatccatc atcttcatct tcgcaggtta tgagacaact  10920
tcatccgtac tgtcattcat tatgtatgaa ttggctactc accctgatgt tcaacagaag  10980
ttacaagaag agattgatgc tgtactgccc aataaggcac cacctaccta cgacactgtc  11040
cttcaaatgg aatacttaga catggttgtc aacgagacat tgagattgtt tccaattgca  11100
atgcgtctgg aaagagtctg caagaaggat gttgaaatca acggtatgtt tatccctaag  11160
ggtgttgtag ttatgatccc atcatacgct ctgcatagag atccaaagta ctggactgaa  11220
```

-continued

```
cctgagaagt tcctgccaga gagattctct aagaagaata aggacaacat agatccctac  11280
atatacactc ccttcggatc tggtccaaga aactgtattg gtatgagatt cgctcttatg  11340
aatatgaagt tagccctgat tagagtctta cagaacttct cctttaagcc atgtaaggaa  11400
acccagatac cactgaaact ttctcttggt ggattgttgc agccagagaa acccgttgtt  11460
ctgaaggtag agtcaagaga tggtacagtg tcaggtgcct gagaattctc atgtaattag  11520
ttatgtcacg cttacattca cgccctcccc ccacatccgc tctaaccgaa aaggaaggag  11580
ttagacaacc tgaagtctag gtccctattt atttttttat agttatgtta gtattaagaa  11640
cgttatttat atttcaaatt tttctttttt ttctgtacag acgcgtgtac gcatgtaaca  11700
ttatactgaa aaccttgctt gagaaggttt tgggacgctc gaaggcttta atttgccgga  11760
ttagaagccg ccgagcgggt gacagccctc cgaaggaaga ctctcctccg tgcgtcctcg  11820
tcttcaccgg tcgcgttcct gaaacgcaga tgtgcctcgc gccgcactgc tccgaacaat  11880
aaagattcta caatactagc ttttatggtt atgaagagga aaaattggca gtaacctggc  11940
cccacaaacc ttcaaatgaa cgaatcaaat taacaaccat aggatgataa tgcgattagt  12000
tttttagcct tatttctggg gtaattaatc agcgaagcga tgatttttga tctattaaca  12060
gatatataaa tgcaaaaact gcataaccac tttaactaat actttcaaca ttttcggttt  12120
gtattacttc ttattcaaat gtaataaaag tatcaacaaa aaattgttaa tatacctcta  12180
tactttaacg tcaaggaggc ggccgccatg tctaaaggtg aagaattatt cactggtgtt  12240
gtcccaattt tggttgaatt agatggtgat gttaatggtc acaaattttc tgtctccggt  12300
gaaggtgaag gtgatgctac ttacggtaaa ttgaccttaa aatttatttg tactactggt  12360
aaattgccag ttccatggcc aaccttagtc actactttcg gttatggtgt tcaatgtttt  12420
gctagatacc cagatcatat gaaacaacat gactttttca agtctgccat gccagaaggt  12480
tatgttcaag aaagaactat ttttttcaaa gatgacggta actacaagac cagagctgaa  12540
gtcaagtttg aaggtgatac cttagttaat agaatcgaat taaaaggtat tgattttaaa  12600
gaagatggta acattttagg tcacaaattg gaatacaact ataactctca caatgtttac  12660
atcatggctg acaaacaaaa gaatggtatc aaagttaact tcaaaattag acacaacatt  12720
gaagatggtt ctgttcaatt agctgaccat tatcaacaaa atactccaat tggtgatggt  12780
ccagtcttgt taccagacaa ccattactta tccactcaat ctgccttatc caaagatcca  12840
aacgaaaaga gagaccacat ggtcttgtta gaatttgtta ctgctgctgg tattacccat  12900
ggtatggatg aattgtacaa ataatctaga gggccgcatc atgtaattag ttatgtcacg  12960
cttacattca cgccctcccc ccacatccgc tctaaccgaa aaggaaggag ttagacaacc  13020
tgaagtctag gtccctattt atttttttat agttatgtta gtattaagaa cgttatttat  13080
atttcaaatt tttctttttt ttctgtacag acgcgtgtac gcatgtaaca ttatactgaa  13140
aaccttgctt gagaaggttt tgggacgctc gaaggcttta atttgcaagc tgcggccctg  13200
cattaatgaa tcggccaacg cgcggggaga ggcggtttgc gtattgggcg ctcttccgct  13260
tcctcgctca ctgactcgct gcgctcggtc gttcggctgc ggcgagcggt atcagctcac  13320
tcaaaggcgg taatacggtt atccacagaa tcaggggata acgcaggaaa gaacatgtga  13380
gcaaaaggcc agcaaaaggc caggaaccgt aaaaaggccg cgttgctggc gtttttccat  13440
aggctccgcc cccctgacga gcatcacaaa aatcgacgct caagtcagag gtggcgaaac  13500
ccgacaggac tataaagata ccaggcgttt ccccctggaa gctccctcgt gcgctctcct  13560
gttccgaccc tgccgcttac cggatacctg tccgcctttc tcccttcggg aagcgtggcg  13620
ctttctcata gctcacgctg taggtatctc agttcggtgt aggtcgttcg ctccaagctg  13680
ggctgtgtgc acgaaccccc cgttcagccc gaccgctgcg ccttatccgg taactatcgt  13740
cttgagtcca acccggtaag acacgactta tcgccactgg cagcagccac tggtaacagg  13800
attagcagag cgaggtatgt aggcggtgct acagagttct tgaagtggtg gcctaactac  13860
ggctacacta gaaggacagt atttggtatc tgcgctctgc tgaagccagt taccttcgga  13920
aaaagagttg gtagctcttg atccggcaaa caaaccaccg ctggtagcgg tggttttttt  13980
gtttgcaagc agcagattac gcgcagaaaa aaaggatctc aagaagatcc tttgatcttt  14040
tctacggggt ctgacgctca gtggaacgaa aactcacgtt aagggatttt ggtcatgaga  14100
ttatcaaaaa ggatcttcac ctagatcctt ttaaattaaa aatgaagttt taaatcaatc  14160
taaagtatat atgagtaaac ttggtctgac agttaccaat gcttaatcag tgaggcacct  14220
atctcagcga tctgtctatt tcgttcatcc atagttgcct gactccccgt cgtgtagata  14280
actacgatac gggagcgctt accatctggc cccagtgctg caatgatacc gcgagaccca  14340
cgctcaccgg ctccagattt atcagcaata aaccagccag ccggaagggc cgagcgcaga  14400
agtggtcctg caactttatc cgcctccatc cagtctatta attgttgccg ggaagctaga  14460
gtaagtagtt cgccagttaa tagtttgcgc aacgttgttg gcattgctac aggcatcgtg  14520
gtgtcactct cgtcgtttgg tatggcttca ttcagctccg gttcccaacg atcaaggcga  14580
gttacatgat cccccatgtt gtgcaaaaaa gcggttagct ccttcggtcc tccgatcgtt  14640
gtcagaagta agttggccgc agtgttatca ctcatggtta tggcagcact gcataattct  14700
cttactgtca tgccatccgt aagatgcttt tctgtgactg gtgagtactc aaccaagtca  14760
ttctgagaat agtgtatgcg gcgaccgagt tgctcttgcc cggcgtcaat acgggataat  14820
agtgtatcac atagcagaac tttaaaagtg ctcatcattg gaaaacgttc ttcggggcga  14880
aaactctcaa ggatcttacc gctgttgaga tccagttcga tgtaacccac tcgtgcaccc  14940
aactgatctt cagcatcttt tactttcacc agcgtttctg ggtgagcaaa aacaggaagg  15000
caaaatgccg caaaaaaggg aataagggcg acacggaaat gttgaatact catactcttc  15060
ctttttcaat gggtaataac tgatataatt aaattgaagc tctaatttgt gagtttagta  15120
tacatgcatt tacttataat acagtttttt agttttgctg gccgcatctt ctcaaatatg  15180
cttcccagcc tgcttttctg taacgttcac cctctacctt agcatccctt ccctttgcaa  15240
atagtcctct tccaacaata ataatgtcag atcctgtaga gaccacatca tccacggttc  15300
tatactgttg acccaatgcg tctcccttgt catctaaacc cacaccgggt gtcataatca  15360
accaatcgta accttcatct cttccaccca tgtctctttg agcaataaag ccgataacaa  15420
aatctttgtc gctcttcgca atgtcaacag taccettagt atattctcca gtagataggg  15480
agcccttgca tgacaattct gctaacatca aaaggcctct aggttccttt gttacttctt  15540
ctgccgcctg cttcaaaccg ctaacaatac ctgggcccac cacaccgtgt gcattcgtaa  15600
tgtctgccca ttctgctatt ctgtatacac ccgcagagta ctgcaatttg actgtattac  15660
caatgtcagc aaattttctg tcttcgaaga gtaaaaaatt gtacttggcg gataatgcct  15720
ttagcggctt aactgtgccc tccatggaaa aatcagtcaa gatatccaca tgtgttttta  15780
gtaaacaaat tttgggacct aatgcttcaa ctaactccag taattccttg gtggtacgaa  15840
catccaatga agcacacaag tttgtttgct tttcgtgcat gatattaaat agcttggcag  15900
caacaggact aggatgagta gcagcacgtt ccttatatgt agctttcgac atgatttatc  15960
```

-continued

```
ttcgtttcct gcaggttttt gttctgtgca gttgggttaa gaatactggg caatttcatg  16020
tttcttcaac actacatatg cgtatatata ccaatctaag tctgtgctcc ttccttcgtt  16080
cttccttctg ttcggagatt accgaatcaa aaaaatttca aagaaaccga aatcaaaaaa  16140
aagaataaaa aaaaaatgat gaattgaatt gaaaagctag cttatcgatg ataagctgtc  16200
aaagatgaga attaattcca cggactatag actatactag atactccgtc tactgtacga  16260
tacacttccg ctcaggtcct tgtcctttaa cgaggcctta ccactctttt gttactctat  16320
tgatccagct cagcaaaggc agtgtgatct aagattctat cttcgcgatg tagtaaaact  16380
agctagaccg agaaagagac tagaaatgca aaaggcactt ctacaatggc tgccatcatt  16440
attatccgat gtgacgctgc agcttctcaa tgatattcga atacgctttg aggagataca  16500
gcctaatatc cgacaaactg ttttacagat ttacgatcgt acttgttacc catcattgaa  16560
ttttgaacat ccgaacctgg gagttttccc tgaaacagat agtatatttg aacctgtata  16620
ataatatata gtctagcgct ttacggaaga caatgtatgt atttcggttc ctggagaaac  16680
tattgcatct attgcatagg taatcttgca cgtcgcatcc ccggttcatt ttctgcgttt  16740
ccatcttgca cttcaatagc atatctttgt taacgaagca tctgtgcttc attttgtaga  16800
acaaaaatgc aacgcgagag cgctaatttt tcaaacaaag aatctgagct gcatttttac  16860
agaacagaaa tgcaacgcga aagcgctatt ttaccaacga agaatctgtg cttcattttt  16920
gtaaaacaaa aatgcaacgc gacgagagcg ctaatttttc aaacaaagaa tctgagctgc  16980
atttttacag aacagaaatg caacgcgaga gcgctatttt accaacaaag aatctatact  17040
tcttttttgt tctacaaaaa tgcatcccga gagcgctatt tttctaacaa agcatcttag  17100
attacttttt ttctcctttg tgcgctctat aatgcagtct cttgataact ttttgcactg  17160
taggtccgtt aaggttagaa gaaggctact ttggtgtcta ttttctcttc cataaaaaaa  17220
gcctgactcc acttcccgcg tttactgatt actagcgaag ctgcgggtgc atttttttcaa  17280
gataaaggca tccccgatta tattctatac cgatgtggat tgcgcatact ttgtgaacag  17340
aaagtgatag cgttgatgat tcttcattgg tcagaaaatt atgaacggtt tcttctattt  17400
tgtctctata tactacgtat aggaaatgtt tacattttcg tattgttttc gattcactct  17460
atgaatagtt cttactacaa tttttttgtc taaagagtaa tactagagat aaacataaaa  17520
aatgtagagg tcgagtttag atgcaagttc aaggagcgaa aggtggatgg gtaggttata  17580
tagggatata gcacagagat atatagcaaa gagatacttt tgagcaatgt ttgtggaagc  17640
ggtattcgca atgggaagct ccaccccggt tgataatcag aaaagcccca aaaacaggaa  17700
gattgtataa gcaaatattt aaattgtaaa cgttaatatt ttgttaaaat tcgcgttaaa  17760
tttttgttaa atcagctcat tttttaacga atagcccgaa atcggcaaaa tcccttataa  17820
atcaaaagaa tagaccgaga tagggttgag tgttgttcca gtttccaaca agagtccact  17880
attaaagaac gtggactcca acgtcaaagg gcgaaaaagg gtctatcagg gcgatggccc  17940
actacgtgaa ccatcaccct aatcaagttt tttggggtcg aggtgccgta aagcagtaaa  18000
tcggaagggt aaacggatgc ccccatttag agcttgacgg ggaaagccgg cgaacgtggc  18060
gagaaaggaa gggaagaaag cgaaaggagc gggggctagg gcggtgggaa gtgtaggggt  18120
cacgctgggc gtaaccacca cacccgccgc gcttaatggg gcgctacagg gcgcgtgggg  18180
atgatccact agt                                                     18193
```